(12) United States Patent
Felfer et al.

(10) Patent No.: US 10,364,257 B2
(45) Date of Patent: Jul. 30, 2019

(54) APPARATUS AND CONTINUOUS FLOW PROCESS FOR PRODUCTION OF BORONIC ACID DERIVATIVES

(71) Applicant: Rempex Pharmaceuticals, Inc., San Diego, CA (US)

(72) Inventors: Ulfried Felfer, Linz (AT); Clemens Stueckler, Graz (AT); Stefan Steinhofer, Enns (AT); Andreas Pelz, Freistadt (AT); Marcus Hanacek, Enns (AT); Thomas Heinrich Pabst, Mintraching (DE); George Winkler, Teublitz (DE); Peter Poechlauer, Linz (AT); Bas Ritzen, Heerlen (NL); Michel Goldbach, Kerkrade (NL)

(73) Assignee: REMPEX PHARMACEUTICALS, INC., Lincolnshire, IL (US)

( * ) Notice: Subject to any disclaimer, the term of this patent is extended or adjusted under 35 U.S.C. 154(b) by 0 days.

(21) Appl. No.: 15/537,378

(22) PCT Filed: Dec. 9, 2015

(86) PCT No.: PCT/US2015/064770
§ 371 (c)(1),
(2) Date: Jun. 16, 2017

(87) PCT Pub. No.: WO2016/100043
PCT Pub. Date: Jun. 23, 2016

(65) Prior Publication Data
US 2017/0369512 A1 Dec. 28, 2017

Related U.S. Application Data

(60) Provisional application No. 62/094,886, filed on Dec. 19, 2014.

(51) Int. Cl.
| | | |
|---|---|---|
| C07F 1/02 | (2006.01) | |
| C07F 5/02 | (2006.01) | |
| C07C 19/03 | (2006.01) | |
| C07D 307/06 | (2006.01) | |

(52) U.S. Cl.
CPC ............ *C07F 5/025* (2013.01); *C07C 19/03* (2013.01); *C07D 307/06* (2013.01); *C07F 1/02* (2013.01)

(58) Field of Classification Search
CPC ....................................................... C07F 5/025
USPC .......................................................... 546/13
See application file for complete search history.

(56) References Cited

U.S. PATENT DOCUMENTS

| | | |
|---|---|---|
| 4,194,047 A | 3/1980 | Christensen et al. |
| 4,260,543 A | 4/1981 | Miller |
| 4,409,214 A | 10/1983 | Takaya et al. |
| 4,822,786 A | 4/1989 | Zama et al. |
| 5,442,100 A | 8/1995 | Bjorkquiest et al. |
| 5,888,998 A | 3/1999 | Maiti et al. |
| 7,271,186 B1 | 9/2007 | Shoichet et al. |
| 8,680,136 B2 * | 3/2014 | Hirst ...................... A61K 31/69 514/438 |
| 9,296,763 B2 | 3/2016 | Hirst et al. |
| 9,511,142 B2 | 12/2016 | Burns et al. |
| 9,694,025 B2 | 7/2017 | Hirst et al. |
| 10,004,758 B2 | 6/2018 | Hirst et al. |
| 2004/0019203 A1 | 1/2004 | Micetich et al. |
| 2012/0040932 A1 | 2/2012 | Hirst et al. |
| 2013/0345172 A1 | 12/2013 | Hirst et al. |
| 2014/0194284 A1 | 7/2014 | Majmudar et al. |
| 2014/0194381 A1 | 7/2014 | Reddy et al. |
| 2014/0194382 A1 | 7/2014 | Reddy et al. |
| 2014/0194384 A1 | 7/2014 | Reddy et al. |
| 2014/0194386 A1 | 7/2014 | Burns et al. |
| 2016/0220591 A1 | 8/2016 | Hirst et al. |
| 2017/0057979 A1 | 3/2017 | Hecker et al. |
| 2018/0071325 A1 | 3/2018 | Hirst et al. |
| 2018/0207183 A1 | 7/2018 | Hirst et al. |
| 2018/0214464 A1 | 8/2018 | Hirst et al. |

FOREIGN PATENT DOCUMENTS

| | | |
|---|---|---|
| WO | WO 1987/05297 | 9/1987 |
| WO | WO 1989/10961 | 11/1989 |
| WO | WO 2009/046098 A1 | 4/2009 |
| WO | WO 2009/064413 A1 | 5/2009 |
| WO | WO 2009/064414 A1 | 5/2009 |
| WO | WO 2010/130708 A1 | 11/2010 |
| WO | WO 2012/021455 A1 | 2/2012 |
| WO | WO 2013/033461 A1 | 3/2013 |
| WO | WO 2013/053372 A1 | 4/2013 |
| WO | WO 2013/122888 A2 | 8/2013 |
| WO | WO 2014/089365 A1 | 6/2014 |
| WO | WO 2015/171430 A1 | 11/2015 |
| WO | WO 2015/191907 A1 | 12/2015 |

OTHER PUBLICATIONS

Brown, J. Org. Chem. 1986,51, 3150-3155.*
Murray, Org. Process Res. Dev. 2013, 17, 1192-1208.*
Wiles, Green Chem., 2012, 14, 38.*
Hafner, Organic Letters (2017), 19(4), 786-789.*
Allen et al., "Ansel's Pharmaceutical Dosage Forms and Drug Delivery Systems", 8th Edition (2004) TOC only.
Arya et al., "Advances in asymmetric enolate methodology", Tetrahedron (2000) 56:917-947.
Banker G.S. et al. [Eds.], Modern Pharmaceutics, 4th Edition; Marcel Dekker, Inc. (2002); Chapters 9 and 10, 98 pages.
Biedrzycki et al., "Derivatives of tetrahedral boronic acids", J. Organomet. Chem. (1992) 431:255-270.

(Continued)

*Primary Examiner* — Nizal S Chandrakumar
(74) *Attorney, Agent, or Firm* — Wilmer Cutler Pickering Hale and Dorr LLP

(57) ABSTRACT

A process for a continuous production of a boronic acid derivative based on a Matteson boronic ester homologation and an apparatus of performing the process are disclosed.

25 Claims, 10 Drawing Sheets

(56) References Cited

OTHER PUBLICATIONS

Bou et al., "Cloning, nucleotide sequencing, and analysis of the gene encoding an AmpC beta-lactamase in Acinetobacter baumannii", Antimicrob Agents Chemother (2000) 44(2):428-432.
Bou et al., "OXA-24, a novel class D beta-lactamase with carbapenemase activity in an Acinetobacter baumannii clinical strain", Antimicrob Agents Chemother (2000) 44(6):1556-1561 and Erratum: Antimicrob Agents Chemother. (2006) 50(6) 2280.
Brosz et al., "Resolution of alpha-aminoboronic esters by diastereoselective crystallization with pinanediols. Confirmation by x-ray analysis", Tetrahedron: Asymmetry (1997) 8(9):1435-1440.
Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2006) M7-A7 26(2), 64 pages.
Clinical and Laboratory Standards Institute (formerly NCCLS, National Committee for Clinical Laboratory Standards). "Methods for Dilution of Antimicrobial Susceptibility Tests for Bacteria That Grow Aerobically", CLSI (Jan. 2009) M07-A8 29(2), 88 pages.
Degennaro et al., "External Trapping of Halomethyllithium Enabled by Flow Microreactors", Adv Synth Catal. (2015) 357: 21-27.
Farquhar et al., "Intensely potent doxorubicin analogues: structure—activity relationship", J. Med. Chem. (1998) 41(6):965-972.
Ghosh et al., "Enantioselective total synthesis of (+)-largazole, a potent inhibitor of histone deacetylase", Org Lett. (2008) 10(17):3907-3909.
Gossinger et al., "Towards EPC-syntheses of the structural class of cochleamycins and macquarimicins. Part 3: EPC-syntheses of the beta-keto lactone subunits and first attempts towards the syntheses of the pentacyclic antibiotics of this group", Tetrahedron (2007) 63:8336-8350.
Ishii et al, "In vitro potentiation of carbapenems with ME1071, a Novel metallo-β-lactamase inhibitor, against metallo-β-lactamase producing pseudomonas aeruginosa clinical isolates." Antimicrob. Agents Chemother. doi:10.1128/AAC.01397-09 (2010) 54(9):3625-3629.
Ito et al., "An efficient constructive method for a tricyclic system: an important intermediate for the synthesis of tricycloclavulone", Tetrahedron Lett. (2003) 44:1259-1261.
Jadhav et al., "Direct synthesis of [alpha-[(tert-Butoxycarbonyl)amino]alkyl]-boronates from (alpha-Haloalkyl)boronates", Org Chem. (1996) 61(22):7951-7954.
Kotha et al., "Recent applications of the suzuki-miyaura cross-coupling reaction in organic synthesis", Tetrahedron (2002) 58:9633-9695.
Kumar et al., "Development of Practical Methodologies for the Synthesis of Functionalized Benzoboroxoles", Tetrahedron Lett. (Aug. 25, 2010) 51(34):4482-4485.
Li et al, "Novel macrocyclic HCV NS3 protease inhibitors derived from α-amino cyclic boronates", Bioorganic Med Chem Lett. (2010) 20:5695-5700.
Li et al., "Synthesis and evaluation of novel alpha-amino cyclic boronates as inhibitors of HCV NS3 protease", Bioorg Med Chem Lett. (2010) 20:3550-3556.

Lieberman H.A. [Ed] *Pharmaceutical Dosage Forms—Tablets; Marcel Dekker, Inc.* (1989) 2nd Ed; TOC.
Matteson, "Boronic esters in stereodirected synthesis", Tetrahedron (1989) 45(7):1859-1885.
Matteson et al., "A stereospecific convergent coupling of nucleophilic and electrophilic chiral carbons", J. Am. Chem. Soc. (1989) 111:4399-4402.
Matteson et al., "Synthesis of asymmetrically deuterated glycerol and dibenzylglyceraldehyde via boronic esters", J. Am. Chem. Soc. (1990) 112:3964-3969.
Meanwell, "Synopsis of some recent tactical application of bioisosteres in drug design", J. Med. Chem. (2011) 54:2529-2591.
Montefour et al., "Acinetobacter baumannii: an emerging multidrug-resistant pathogen in a critical care", Crit Care Nurse (2008) 28(1):15-25.
Morandi et al., "Structure-based optimization of cephalothin-analogue boronic acids as beta-lactamase inhibitors", Bioorg Med Chem. (2008) 16(3):1195-205. Epub Nov. 7, 2007.
Nema et al., "Excipients and Their Role in Approved Injectable Products: Current Usage and Future Directions", PDA J Pharm Sci Technol. (2011) 65(3):287-332.
Panek et al., "Diastereoselectivity in the borane methyl sulfide promoted hydroboration of .alpha.-alkoxy-.beta, gamma.-unsaturated esters. Documentation of an alkoxy-directed hydroboration reaction", J. Org. Chem. (1992) 57(20):5288-5290.
Perez et al., "Why are we afraid of Acinetobacter baumannii?", Expert Rev Anti Infect Ther. (2008) 6(3):269-71.
Powell et al., "Compendium of excipients for parenteral formulations", PDA J Pharm Sci Technol. (1998) 52(5):238-311.
Reissig et al.,"High diastereoselection in the alkylation of siloxy-substituted methyl cyclopropanecarboxylates: consequence of a pyramidal ester enolate anion?", J. Am. Chem. Soc. (1982) 104:1735-1737.
Sawyer et al., "Physical properties and synthetic utility of a-alkoxyorganolithium species as studied through ligand selectivity in tin-lithium exchange", J. Am. Chem. Soc. (1988) 110:842-853.
Souto et al., "Synthesis and biological characterization of the histone deacetylase inhibitor largazole and c7-modified analogues", J. Med. Chem. (2010) 53(12):4654-4667.
Spiegel et al., "CP-263,114 synthetic studies. Construction of an isotwistane ring system via rhodium carbenoid C-H insertion", Tetrahedron (2002) 58:6545-6554.
Wohlrab et al., "Total synthesis of plusbacin A3: a depsipeptide antibiotic active against 66 vancomycin-resistant bacteria", J. Am. Chem. Soc. (2007) 129:4175-4177.
Yamamoto et al., "Iridium-catalyzed hydroboration of alkenes with pinacolborane", Tetrahedron (2004) 60:10695-10700.
International Search Report and Written Opinion dated Mar. 16, 2016 for Application No. PCT/US2015/064770, filed Dec. 9, 2015.
Larock R. [Ed.] *Comprehensive Organic Transformations*, VCH Publishers 1989; TOC, 11 pages.
Paquette L.A. [Ed.] *Encyclopedia of Reagents for Organic Synthesis*, vol. 1; J. Wiley & Sons (1995); Cover Only.
European Extended Search Report dated May 25, 2018 for corresponding Application No. 15870720.8, filed Jul. 18, 2017.

* cited by examiner

APPARATUS AND CONTINUOUS FLOW PROCESS FOR PRODUCTION OF BORONIC ACID DERIVATIVES

INCORPORATION BY REFERENCE TO ANY PRIORITY APPLICATION

This application is the U.S. National Phase of International Application No. PCT/US2015/064770 entitled APPARATUS AND CONTINUOUS FLOW PROCESS FOR PRODUCTION OF BORONIC ACID DERIVATIVES, filed on Dec. 9, 2015 and published on Jun. 23, 2016 as WO 2016/100043, which claims the benefit of U.S. Provisional Application No. 62/094,886, entitled Apparatus and Continuous Flow Process for Production of Boronic Acid Derivatives, filed Dec. 19, 2014, the disclosure of which is incorporated herein by reference in its entirety.

BACKGROUND OF THE INVENTION

Field

The present disclosure relates to a continuous flow process for production of boronic acid derivatives and apparatus of performing the same. More particularly, it relates to a continuous flow process for a large scale production of boronic acid derivatives.

Description of the Related Art

Boronic acid derivatives are useful as potentiators of antimicrobial compounds. Some methods for boronic ester synthesis include the homologation of boronic esters by addition of a dichloroalkyllithium reagent, forming an intermediate boronate complex in the presence of a Lewis acid catalyst. The Lewis acid promotes the rearrangement reaction and minimizes epimerization at the alpha-carbon atom. However, maintenance of very low temperature (≤−90° C.), exclusion of water and careful control of Lewis acid stoichiometry are required for good results. These features render the reaction difficult to perform successfully on a production scale, and limit the availability of pharmaceutically important boronic ester and acid compounds. Thus, there remains a need for a process for the large-scale production of boronic acid derivatives.

SUMMARY

Some embodiments disclosed herein include a process for production of a compound of Formula (Ia) or (Ib),

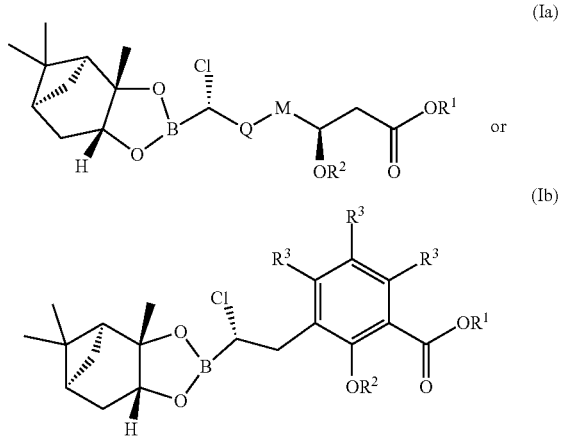

wherein:
Q is —$(CH_2)_n$—;
M is —$CH_2$— or —CH=CH—;
n is 1 or 2;
$R^1$ is a carboxyl protecting group;
$R^2$ is a hydroxyl protecting group; or
$R^1$ and $R^2$ together with the atoms to which they are attached form a five-member heterocyclic ring optionally substituted with $C_{1-4}$ alkyl;
each $R^3$ is independently selected from hydrogen, —OH, halogen, —$CF_3$, $C_1$-$C_6$ alkenyl, $C_1$-$C_6$ alkynyl, $C_1$-$C_6$ heteroalkyl, $C_3$-$C_7$ carbocyclyl, 5-10 membered heterocyclyl, $C_6$-$C_{10}$ aryl, 5-10 membered heteroaryl, cyano, $C_1$-$C_6$ alkoxy($C_1$-$C_6$)alkyl, $C_6$-$C_{10}$ aryloxy, sulfhydryl (mercapto), and —$(CH_2)_m$—Y'—$(CH_2)_p$M';
m and p are independently 0 to 3;
Y' is selected from the group consisting of —S—, —S(O)—, —$S(O)_2$—, —O—, —$CR^{4a}R^{5a}$—, and —$NR^{1a}$—;
M' is selected from the group consisting of —C(O) $NR^{1a}R^{2a}$; —C(O)$NR^{1a}OR^{3a}$; —$NR^{1a}C(O)R^{4a}$; —$NR^1C(O)NR^{2a}R^{1b}$; —$NR^1C(O)OR^{3a}$; —$NR^1S(O)_2R^{3a}$; —$NR^{1a}S(O)_2NR^{2a}R^{1b}$; —C(=$NR^{1a}$)$NR^{4a}$; —C(=$NR^{1a}$)$NR^{2a}R^{1b}$; —$NR^{1a}CR^{4a}$(=$NR^{2a}$); —$NR^{1a}C$(=$NR^{2a}$)$NR^{1b}R^{2b}$; $C_{1-4}$ alkyl optionally substituted with 0-2 substituents selected from the group consisting, —$OR^{3a}$, —$NR^{1a}R^{2a}$, halogen, —C(O) $NR^{1a}R^{2a}$, and —$NR^{1a}C(O)R^{4a}$; $C_{3-10}$ cycloalkyl optionally substituted with 0-2 substituents selected from the group consisting of $C_{1-4}$ alkyl, —$OR^{3a}$, —$NR^{1a}R^{2a}$, halogen, —C(O)$NR^{1a}R^{2a}$, and —$NR^{1a}C$(O)$R^{4a}$; $C_{6-10}$ aryl optionally substituted with 0-2 substituents selected from the group consisting of $C_{1-4}$ alkyl, —$OR^{3a}$, —$NR^{1a}R^{2a}$, halogen, —C(O)$NR^{1a}R^{2a}$, and —$NR^{1a}C(O)R^{4a}$; 5 to 10 membered heteroaryl optionally substituted with 0-2 substituents selected from the group consisting of $C_{1-4}$ alkyl, —$OR^{3a}$, —$NR^{1a}R^{2a}$, halogen, —C(O)$NR^{1a}R^{2a}$, and —$NR^{1a}C$(O)$R^{4a}$; and 4 to 10 membered heterocyclyl optionally substituted with 0-2 substituents selected from the group consisting of $C_{1-4}$ alkyl, —$OR^{3a}$, —$NR^{1a}R^{2a}$, halogen, —C(O)$NR^{1a}R^{2a}$, and —$NR^{1a}C(O)R^{4a}$;
each $R^{1a}$, $R^{2a}$, $R^{1b}$ and $R^{2b}$ are independently selected from the group consisting of —H, optionally substituted —$C_{1-10}$alkyl, optionally substituted $C_{2-10}$alkenyl, optionally substituted $C_{2-10}$alkynyl, optionally substituted $C_{3-7}$ cycloalkyl, optionally substituted 3-8 membered heterocyclyl, optionally substituted $C_{6-10}$aryl, and optionally substituted 5-10 membered heteroaryl;
$R^{3a}$ is hydrogen, optionally substituted $C_{1-10}$alkyl, —optionally substituted $C_{1-10}$alkyl-COOH, optionally substituted $C_{2-10}$alkenyl, optionally substituted $C_{2-10}$alkynyl, optionally substituted $C_{3-7}$ cycloalkyl, optionally substituted 3-8 membered heterocyclyl, optionally substituted $C_{6-10}$aryl, and optionally substituted 5-10 membered heteroaryl; and
each $R^{4a}$ and $R^{5a}$ is independently selected from the group consisting of —H, —OH, —optionally substituted alkoxyl, optionally substituted —$C_{1-10}$alkyl, optionally substituted $C_{2-10}$alkenyl, optionally substituted $C_{2-10}$alkynyl, optionally substituted $C_{3-7}$ cycloalkyl, optionally substituted 3-8 membered heterocyclyl, optionally substituted $C_{6-10}$aryl, and optionally substituted 5-10 membered heteroaryl;
the process comprising:
providing a first continuous flow of alkyl lithium;
providing a continuous flow of dichloromethane;

combining the first continuous flow of alkyl lithium and the continuous flow of dichloromethane at an input of a first continuous flow conduit to yield a continuous flow of a first reaction intermediate at an output of the first continuous flow conduit;

providing a continuous flow of a compound of Formula (IIa) or (IIb);

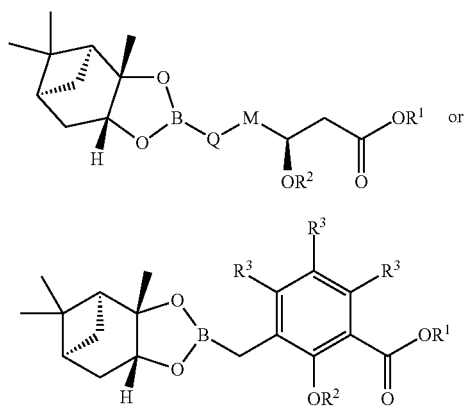

combining the continuous flow of the first reaction intermediate and the continuous flow of the compound of Formula (IIa) or (IIb) at an input of the a second continuous flow conduit to yield a second reaction intermediate at an output of the second continuous flow conduit; and collecting the second reaction intermediate at the output of the second continuous flow conduit and treating with a Lewis acid to yield the compound of Formula (Ia) or (Ib).

Some embodiments disclosed herein include an apparatus for production of a compound of Formula Ia or Ib,

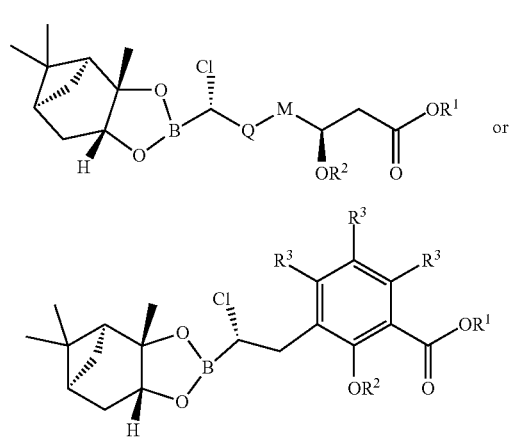

wherein:
Q is —$(CH_2)_n$—;
M is —$CH_2$— or —CH=CH—;
n is 1 or 2;
$R^1$ is a carboxyl protecting group;
$R^2$ is a hydroxyl protecting group; or
$R^1$ and $R^2$ together with the atoms to which they are attached form a five-member heterocyclic ring optionally substituted with $C_{1-4}$ alkyl;

each $R^3$ is independently selected from hydrogen, —OH, halogen, —$CF_3$, $C_1$-$C_6$ alkenyl, $C_1$-$C_6$ alkynyl, $C_1$-$C_6$ heteroalkyl, $C_3$-$C_7$ carbocyclyl, 5-10 membered heterocyclyl, $C_6$-$C_{10}$ aryl, 5-10 membered heteroaryl, cyano, $C_1$-$C_6$ alkoxy($C_1$-$C_6$)alkyl, $C_6$-$C_{10}$ aryloxy, sulfhydryl (mercapto), and —$(CH_2)_m$—Y'—$(CH_2)_p$M';

m and p are independently 0 to 3;

Y' is selected from the group consisting of —S—, —S(O)—, —S(O)$_2$—, —O—, —$CR^{4a}R^{5a}$—, and —$NR^{1a}$—;

M' is selected from the group consisting of —C(O)$NR^{1a}R^{2a}$; —C(O)$NR^{1a}OR^{3a}$; $NR^{1a}C(O)R^{4a}$; —$NR^1C(O)NR^{2a}R^{1b}$; —$NR^1C(O)OR^{3a}$; —$NR^1S(O)_2R^{3a}$; $NR^{1a}S(O)_2NR^{2a}R^{1b}$; —C(=$NR^{1a}$)$R^{4a}$; —C(=$NR^{1a}$)$NR^{2a}R^{1b}$; —$NR^{1a}CR^{4a}$(=$NR^{2a}$); —$NR^{1a}C$(=$NR^{2a}$)$NR^{1b}R^{2b}$; $C_{1-4}$ alkyl optionally substituted with 0-2 substituents selected from the group consisting, —$OR^{3a}$, —$NR^{1a}R^{2a}$, halogen, —C(O)$NR^{1a}R^{2a}$, and —$NR^{1a}C(O)R^{4a}$; $C_{3-10}$ cycloalkyl optionally substituted with 0-2 substituents selected from the group consisting of $C_{1-4}$ alkyl, —$OR^{3a}$, —$NR^{1a}R^{2a}$, halogen, —C(O)$NR^{1a}R^{2a}$, and —$NR^{1a}C(O)R^{4a}$; $C_{6-10}$ aryl optionally substituted with 0-2 substituents selected from the group consisting of $C_{1-4}$ alkyl, —$OR^{3a}$, —$NR^{1a}R^{2a}$, halogen, —C(O)$NR^{1a}R^{2a}$, and —$NR^{1a}C(O)R^{4a}$; 5 to 10 membered heteroaryl optionally substituted with 0-2 substituents selected from the group consisting of $C_{1-4}$ alkyl, —$OR^{3a}$, —$NR^{1a}R^{2a}$, halogen, —C(O)$NR^{1a}R^{2a}$, and —$NR^{1a}C(O)R^{4a}$; and 4 to 10 membered heterocyclyl optionally substituted with 0-2 substituents selected from the group consisting of $C_{1-4}$ alkyl, —$OR^{3a}$, —$NR^{1a}R^{2a}$, halogen, —C(O)$NR^{1a}R^{2a}$, and —$NR^{1a}C(O)R^{4a}$;

each $R^{1a}$, $R^{2a}$, $R^{1b}$ and $R^{2b}$ are independently selected from the group consisting of —H, optionally substituted —$C_{1-10}$alkyl, optionally substituted $C_{2-10}$alkenyl, optionally substituted $C_{2-10}$alkynyl, optionally substituted $C_{3-7}$ cycloalkyl, optionally substituted 3-8 membered heterocyclyl, optionally substituted $C_{6-10}$aryl, and optionally substituted 5-10 membered heteroaryl;

$R^{3a}$ is hydrogen, optionally substituted $C_{1-10}$alkyl, —optionally substituted $C_{1-10}$alkyl-COOH, optionally substituted $C_{2-10}$alkenyl, optionally substituted $C_{2-10}$alkynyl, optionally substituted $C_{3-7}$ cycloalkyl, optionally substituted 3-8 membered heterocyclyl, optionally substituted $C_{6-10}$aryl, and optionally substituted 5-10 membered heteroaryl; and each $R^{4a}$ and $R^{5a}$ is independently selected from the group consisting of —H, —OH, —optionally substituted alkoxyl, optionally substituted —$C_{1-10}$alkyl, optionally substituted $C_{2-10}$alkenyl, optionally substituted $C_{2-10}$alkynyl, optionally substituted $C_{3-7}$ cycloalkyl, optionally substituted 3-8 membered heterocyclyl, optionally substituted $C_{6-10}$aryl, and optionally substituted 5-10 membered heteroaryl;

the apparatus comprising:
a first vessel having an output and comprising alkyl lithium;
a second vessel having an output and comprising dichloromethane;
a first continuous flow conduit comprising an input and an output, wherein the input of the first continuous flow conduit is fluidly coupled to the output of the first vessel and the output of the second vessel;
a third vessel having an output and comprising a compound of Formula (IIa) or (IIb);

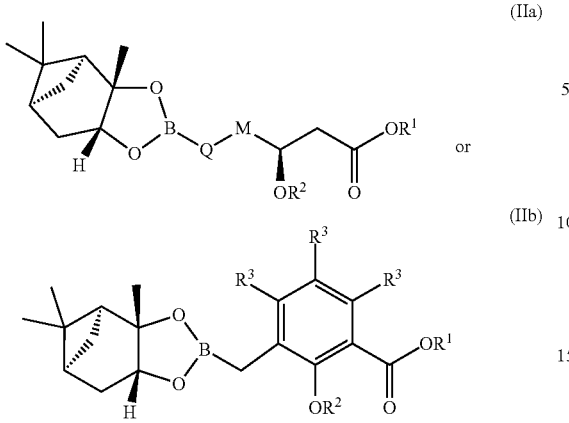

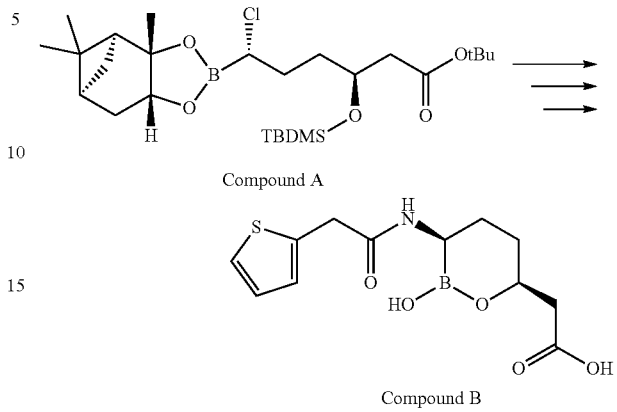

a second continuous conduit comprising an input and an output, wherein the input of the second continuous conduit is fluidly coupled to the output of the first continuous flow conduit and the output of the third vessel;

a fourth vessel having an input fluidly coupled to the output of the second continuous flow conduit and comprising a Lewis acid.

BRIEF DESCRIPTION OF THE DRAWINGS

FIG. 3A shows the HPLC traces of the reaction mixture collected the experiment 2.2; FIG. 3B shows the HPLC traces of the reaction mixture collected the experiments 3.2.

DETAILED DESCRIPTION OF THE PREFERRED EMBODIMENT

Figure 1:
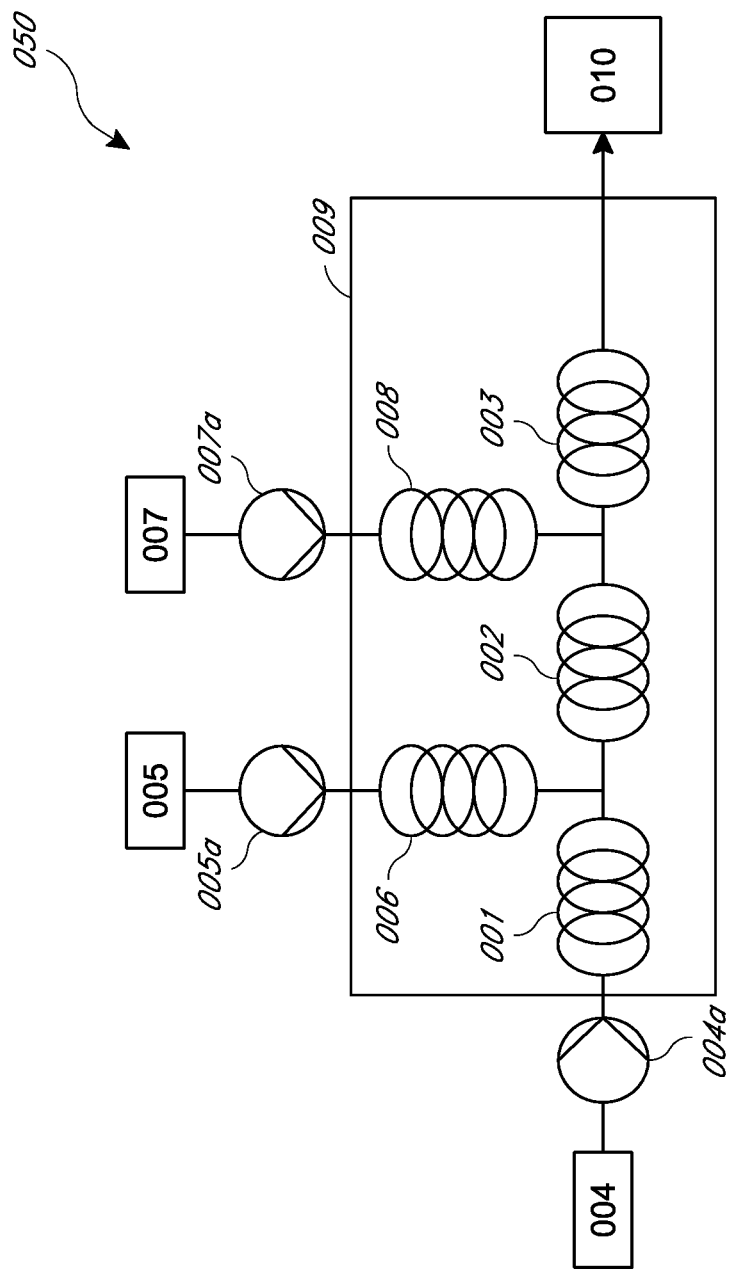
FIG. 1 is a non-limiting schematic of the continuous flow apparatus.

The disclosed technology relates to a continuous flow process for the production of boronic acid derivatives. Using stainless steel tubular reaction apparatus, the process allows the production of boronic acid derivatives such as the compound described herein with a high yield and high selectivity. In some embodiments, the process operates under cryogenic conditions; however, reaction temperatures below −90° C. used for batch production can be avoided. In some embodiments, temperatures of −80° C. to −65° C. can be used to provide a more readily scalable process with better reproducibility and higher yield. This continuous flow process can be used in large scale production.

The chiral boronic ester compound A is an intermediate in the synthesis of Compound B, a β-lactamase inhibitor.

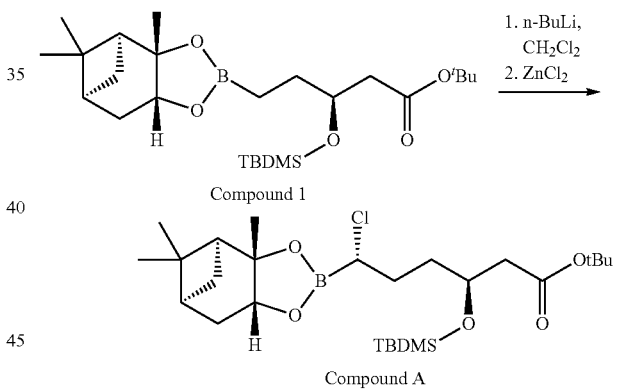

The existing batch process for synthesis of Compound A involves a Matteson boronic ester homologation of compound 1 (scheme 1). The lability of the lithiated species involved requires this reaction to be performed under cryogenic conditions (−95° C.), which is a challenge from a scalability point of view.

Scheme 1. Synthesis of compound A via Matteson boronic ester homologation

In addition, in a batch process, all the operations are performed in successive steps using one or more reactors, and the increase in production scale in a batch production often results in lower yield, higher level of impurities, and poor reproducibility and selectivity for stereoisomers. In addition, large reactor volumes also may correspond to increase in capital investments.

In a continuous process, separate continuous flow conduits are used for each step of the reaction, and the reaction mixture flows from one operation to the next within the production line. The operations are performed continuously and some of the reaction parameters such as flow rate, molar ratio, and reaction temperatures can be easily and quickly adjusted based on a concurrent monitoring of the reaction product. Consequently, a continuous production process requires much smaller equipment volumes for achieving the same production capacity. In addition, a continuous operation helps to ensure the quality of the product. Moreover, a continuous flow process may be preferable over a traditional batch process as it would mitigate the risks that are associated with potentially hazardous decomposition reactions of the lithium salt of dichloromethane. Furthermore, the shorter residence times in continuous flow set-up can allow operation at higher temperatures.

A continuous flow process and the apparatus for performing the continuous flow process are often complicated to design and highly specific to the types of reaction product and production rate. The continuous flow process described herein, by utilizing a continuous flow process to produce a reaction intermediate and performing the last quenching step in a non-continuous-flow vessel, has shown great reproducibility and high yield as compared to the other types continuous flow processes that involve performing the last quenching step inside a continuous flow conduit. Additionally, the continuous flow process described herein has allowed successful production of compound of formula I, particularly compound A, in a scale of over 880 kg with an average yield of over 90%.

Definitions

The term "substantially free of water" as used herein means a product has been dried using standard techniques known in the art. In some embodiments, "substantially free of water" means the product contains less than 0.5%, 1%, 3%, or 5% of water. In some embodiments, "substantially free of water" means the product contains less than 0.1% of water or no water.

The term "continuous flow conduit" as used herein refers to any pipe, tube, channel, channeled plate, or any other vessel of suitable shape for conveying fluids in a continuous flow process.

The term "residence time" as used herein refers to the time required for the reaction mixture or stock solution to flow from the input to the output of a continuous flow conduit.

The term "thermally coupled" as used herein refers to a direct or indirect coupling between two objects in way that facilitates heat transfer between the two objects. For example, when a vessel or continuous flow conduit is thermally coupled to a cooling bath, the vessel or continuous flow conduit can be immersed in the cooling bath to achieve a desired temperature.

The term "fluidly coupled" as used herein means that a first component are in fluid communication with another component. Such fluid communication may be achieved by either direct or indirect connection via valves, pipes, conveyors, pumps, conduits and any other suitable connectors known by those skilled in the art.

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$ and $(CH_3)_3C-$.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group of the compounds may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, iso-butylmercapto, sec-butylmercapto, tert-butylmercapto, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group of the compounds may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group of the compounds may be designated as "$C_{2-4}$ alkynyl" or similar designations. By way of example only, "$C_{2-4}$ alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atoms although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group of the compounds may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" refers to RO— and RS—, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinolinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidinyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. A non-limiting example includes carboxyl (i.e., —C(=O)OH).

A "cyano" group refers to a "—CN" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "sulfonyl" group refers to an "—$SO_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "S-sulfonamido" group refers to a "—$SO_2NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-sulfonamido" group refers to a "—$N(R_A)SO_2R_B$" group in which $R_A$ and $R_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-carbamyl" group refers to a "—$OC(=O)NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-carbamyl" group refers to an "—$N(R_A)OC(=O)R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-thiocarbamyl" group refers to a "—$OC(=S)NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, a $C_{6-10}$ aryl, 5-10 membered heteroaryl, and 5-10 membered heterocyclyl, as defined herein.

An "N-thiocarbamyl" group refers to an "—$N(R_A)OC(=S)R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-amido" group refers to a "—$C(=O)NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-amido" group refers to a "—$N(R_A)C(=O)R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$)alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

In some embodiments, substituted group(s) is (are) substituted with one or more substituent(s) individually and independently selected from $C_1$-$C_4$ alkyl, amino, hydroxy, and halogen.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH$_2$—, —CH$_2$CH$_2$—, —CH$_2$CH(CH$_3$)CH$_2$—, and the like. Other radical naming conventions clearly indicate that the radical is a di-radical such as "alkylene" or "alkenylene."

As used herein, "alkylene" means a branched, or straight chain fully saturated di-radical chemical group containing only carbon and hydrogen that is attached to the rest of the molecule via two points of attachment (i.e., an alkanediyl). The alkylene group may have 1 to 20 carbon atoms, although the present definition also covers the occurrence of the term alkylene where no numerical range is designated. The alkylene group may also be a medium size alkylene having 1 to 9 carbon atoms. The alkylene group could also be a lower alkylene having 1 to 4 carbon atoms. The alkylene group may be designated as "C$_{1-4}$ alkylene" or similar designations. By way of example only, "C$_{1-4}$ alkylene" indicates that there are one to four carbon atoms in the alkylene chain, i.e., the alkylene chain is selected from the group consisting of methylene, ethylene, ethan-1,1-diyl, propylene, propan-1,1-diyl, propan-2,2-diyl, 1-methyl-ethylene, butylene, butan-1,1-diyl, butan-2,2-diyl, 2-methyl-propan-1,1-diyl, 1-methyl-propylene, 2-methyl-propylene, 1,1-dimethyl-ethylene, 1,2-dimethyl-ethylene, and 1-ethyl-ethylene.

As used herein, "alkenylene" means a straight or branched chain di-radical chemical group containing only carbon and hydrogen and containing at least one carbon-carbon double bond that is attached to the rest of the molecule via two points of attachment. The alkenylene group may have 2 to 20 carbon atoms, although the present definition also covers the occurrence of the term alkenylene where no numerical range is designated. The alkenylene group may also be a medium size alkenylene having 2 to 9 carbon atoms. The alkenylene group could also be a lower alkenylene having 2 to 4 carbon atoms. The alkenylene group may be designated as "C$_{2-4}$ alkenylene" or similar designations. By way of example only, "C$_{2-4}$ alkenylene" indicates that there are two to four carbon atoms in the alkenylene chain, i.e., the alkenylene chain is selected from the group consisting of ethenylene, ethen-1,1-diyl, propenylene, propen-1,1-diyl, prop-2-en-1,1-diyl, 1-methyl-ethenylene, but-1-enylene, but-2-enylene, but-1,3-dienylene, buten-1,1-diyl, but-1,3-dien-1,1-diyl, but-2-en-1,1-diyl, but-3-en-1,1-diyl, 1-methyl-prop-2-en-1,1-diyl, 2-methyl-prop-2-en-1,1-diyl, 1-ethyl-ethenylene, 1,2-dimethyl-ethenylene, 1-methyl-propenylene, 2-methyl-propenylene, 3-methyl-propenylene, 2-methyl-propen-1,1-diyl, and 2,2-dimethyl-ethen-1,1-diyl.

Continuous Production Process

One aspect of the present technology relates to a process for production of a compound of Formula (Ia) or (Ib),

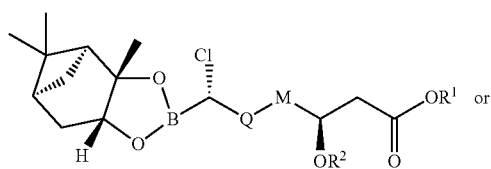
(Ia)

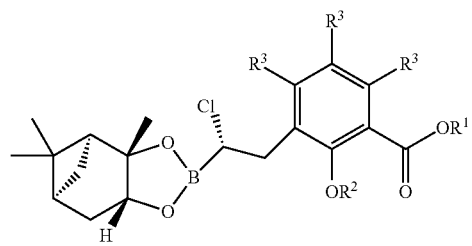
(Ib)

the process comprising:
providing a first continuous flow of alkyl lithium;
providing a continuous flow of dichloromethane;
combining the first continuous flow of alkyl lithium and the continuous flow of dichloromethane at an input of a first continuous flow conduit to yield a continuous flow of a first reaction intermediate at an output of the first continuous flow conduit;
providing a continuous flow of a compound of Formula (IIa) or (IIb);

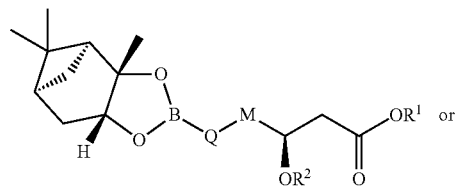
(IIa)

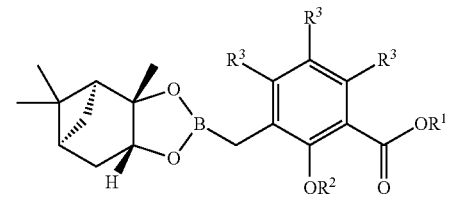
(IIb)

combining the continuous flow of the first reaction intermediate and the continuous flow of the compound of Formula (IIa) or (IIb) at an input of the a second continuous flow conduit to yield a second reaction intermediate at an output of the second continuous flow conduit; and
collecting the second reaction intermediate at the output of the second continuous flow conduit and treating with a Lewis acid to yield the compound of Formula (Ia) or (Ib).

In some embodiments, the second reaction intermediate is collected in a vessel wherein the vessel does not have a continuous outflow. In some embodiments, the second reaction intermediate is collected in a vessel wherein the vessel is a continuous outflow or includes at least one continuous flow.

The first continuous flow of alkyl lithium can be a continuous flow of alkyl lithium in one or more suitable organic solvents. In some embodiments, the first continuous flow of alkyl lithium is a continuous flow of alkyl lithium in heptane, hexane, cyclohexane, toluene, or any combinations thereof. In some embodiments, the first continuous flow of alkyl lithium is a continuous flow of alkyl lithium in tetrahydrofuran and at least one additional solvent selected from heptane, cyclohexane, toluene, or combinations thereof. In some embodiments, the first continuous flow of alkyl lithium is a continuous flow of alkyl lithium in hexane and tetrahydrofuran. In some embodiments, the first continuous flow of alkyl lithium is a continuous flow of alkyl lithium in hexane. In some embodiments, the first continuous flow of alkyl lithium is a continuous flow of alkyl lithium in tetrahydrofuran.

In some embodiments, the providing a first continuous flow of alkyl lithium further comprises
providing a continuous flow of tetrahydrofuran;
providing a second continuous flow of alkyl lithium; and
combining the continuous flow of tetrahydrofuran and the second continuous flow of alkyl lithium at an input of a third continuous flow conduit to form the first continuous flow of alkyl lithium.

The second continuous flow of alkyl lithium can be in one or more suitable solvents. In some embodiments, the second continuous flow of alkyl lithium is in heptane.

The continuous flow of dichloromethane can be a continuous flow of dichloromethane in one or more organic solvents. In some embodiments, the continuous flow of dichloromethane is a continuous flow of dichloromethane in tetrahydrofuran.

The continuous flow of the compound of Formula (IIa) or (IIb) can be a continuous flow of the compound of Formula (IIa) or (IIb) in one or more suitable organic solvents. In some embodiments, the continuous flow of the compound of Formula (IIa) or (IIb) is a continuous flow of the compound of Formula (IIa) or (IIb) in heptane. In some embodiments, the continuous flow of the compound of Formula (IIa) or (IIb) is a continuous flow of the compound of Formula (IIa) or (IIb) in tetrahydrofuran. In some embodiments, the continuous flow of the compound of Formula (IIa) or (IIb) is a continuous flow of the compound of Formula (IIa) or (IIb) in heptane and tetrahydrofuran. In some embodiments, the providing a continuous flow of a compound of formula (IIa) or (IIb) further comprises combining the compound of formula (IIa) or (IIb) in heptane with tetrahydrofuran.

The process described herein can further include preparing the reagents or solvents used in the process under an inert atmosphere. In some embodiments, the process described herein can further include preparing the alkyl lithium, the dichloromethane, the compound of formula (IIa) or (IIb), the Lewis acid, and the tetrahydrofuran under a nitrogen or argon atmosphere.

The reagents and solvents used in this process can be substantially free of water. In some embodiments, the alkyl lithium, the dichloromethane, the compound of formula (IIa) or (IIb), the Lewis acid, the Lewis acid, and the tetrahydrofuran used in the process are substantially free of water.

The process can further include pre-cooling the alkyl lithium to a temperature suitable for the Matteson reaction. The pre-cooling process can include one or more stages of gradually lowering the temperature. For example, the pre-cooling described herein can include a first stage of lowering the temperature and a second stage of further lowering the temperature. In some embodiments, the process described herein can further include pre-cooling the alkyl lithium to a temperature in the range of about −100° C. to about 0° C. prior to the combining of the first continuous flow of alkyl lithium and the continuous flow of dichloromethane. In some embodiments, the process described herein can further include pre-cooling the alkyl lithium to a temperature of about −90° C., −80° C., −75° C., −70° C., −65° C., −60° C., −50° C., −40° C., −30° C., −25° C., −10° C., or −5° C. prior to the combining of the first continuous flow of alkyl lithium and the continuous flow of dichloromethane. In some embodiments, the process described herein can further include a first stage of pre-cooling the alkyl lithium to a temperature of about −20° C. prior to the combining of the first continuous flow of alkyl lithium and the continuous flow of dichloromethane. In some embodiments, the process described herein can further include a first stage of pre-cooling the alkyl lithium to a temperature of about −40° C. prior to the combining of the first continuous flow of alkyl lithium and the continuous flow of dichloromethane. In some embodiments, the process described herein can further include a first stage of pre-cooling the alkyl lithium to a temperature of about −60° C. prior to the combining of the first continuous flow of alkyl lithium and the continuous flow of dichloromethane. In some embodiments, the process described herein can further include pre-cooling the alkyl lithium to a temperature of about −65° C. prior to the combining of the first continuous flow of alkyl lithium and the continuous flow of dichloromethane. In some embodiments, the process described herein can further include pre-cooling the alkyl lithium to a temperature of about −70° C. prior to the combining of the first continuous flow of alkyl lithium and the continuous flow of dichloromethane. In some embodiments, the process described herein can further include pre-cooling the alkyl lithium to a temperature of about −75° C. prior to the combining of the first continuous flow of alkyl lithium and the continuous flow of dichloromethane. In some embodiments, the process described herein can further include pre-cooling the alkyl lithium to a temperature in the range of about −75° C. to −60° C. prior to the combining of the first continuous flow of alkyl lithium and the continuous flow of dichloromethane. In some embodiments, the process described herein can further include pre-cooling the alkyl lithium to a temperature in the range of about −80° C. to −65° C. prior to the combining of the first continuous flow of alkyl lithium and the continuous flow of dichloromethane. In some embodiments, the process described herein can further include pre-cooling the alkyl lithium to a temperature in the range of about −85° C. to −60° C. prior to the combining of the first continuous flow of alkyl lithium and the continuous flow of dichloromethane.

In an embodiment wherein a continuous flow of tetrahydrofuran is provided separately from the alkyl lithium heptane, the process described herein can further comprise pre-cooling the tetrahydrofuran. In some embodiments, the tetrahydrofuran can be pre-cooled to a temperature in the range of about −85° C. to −60° C. prior to being combined with the separate continuous flow of alkyl lithium. In some embodiments, the tetrahydrofuran can be pre-cooled to a temperature in the range of about −80° C. to −65° C. prior to being combined with the separate continuous flow of alkyl lithium. In some embodiments, the tetrahydrofuran can be pre-cooled to a temperature of about −80° C., −75° C., −70° C., −65° C., or −60° C. prior to the being combined with the continuous flow of tetrahydrofuran and the second continuous flow of alkyl lithium.

In such an embodiment, the process described herein can further comprise pre-cooling the separate continuous flow of alkyl lithium. In such an embodiment, the separate continuous flow of alkyl lithium can be pre-cooled to a temperature in the range of about −85° C. to −60° C. prior to being combined with the continuous flow of tetrahydrofuran. In some embodiments, the separate continuous flow of alkyl lithium can be pre-cooled to a temperature in the range of about −80° C. to −65° C. prior to being combined with the continuous flow of tetrahydrofuran. In some embodiments, the separate continuous flow of alkyl lithium can be pre-cooled to a temperature of about −80° C., −75° C., −70° C., −65° C., or −60° C. prior to being combined with the continuous flow of tetrahydrofuran.

The process can further include pre-cooling the dichloromethane to a temperature suitable for the Matteson reaction. In some embodiments, the process described herein can further include pre-cooling the dichloromethane to a temperature in the range of about −100° C. to about 0° C. prior to the combining of the first continuous flow of alkyl lithium and the continuous flow of dichloromethane. In some embodiments, the process described herein can further include pre-cooling the dichloromethane to a temperature of about −90° C., −80° C., −75° C., −70° C., −65° C., −60° C., −55° C., −50° C., −40° C., −30° C., −20° C., −10° C., or −5° C. prior to the combining of the first continuous flow of alkyl lithium and the continuous flow of dichloromethane. In some embodiments, the process described herein can further include pre-cooling the dichloromethane to a temperature of about −60° C. prior to the combining of the first continuous flow of alkyl lithium and the continuous flow of dichloromethane. In some embodiments, the process described herein can further include pre-cooling the dichloromethane to a temperature in the range of about −75° C. to −60° C. prior to the combining of the first continuous flow of alkyl lithium and the continuous flow of dichloromethane. In some embodiments, the process described herein can further include pre-cooling the dichloromethane to a temperature in the range of about −80° C. to −65° C. prior to the combining of the first continuous flow of alkyl lithium and the continuous flow of dichloromethane. In some embodiments, the process described herein can further include pre-cooling the dichloromethane to a temperature in the range of about −85° C. to −60° C. prior to the combining of the first continuous flow of alkyl lithium and the continuous flow of dichloromethane.

The process can further include pre-cooling the compound of Formula (IIa) or (IIb) to a temperature suitable for the Matteson reaction. In some embodiments, the process described herein can further include pre-cooling the compound of Formula (IIa) or (IIb) to a temperature in the range of about −100° C. to about 0° C. prior to the combining of the continuous flow of the first reaction intermediate and the continuous flow of the compound of Formula (IIa) or (IIb). In some embodiments, the process described herein can further include pre-cooling the compound of Formula (IIa) or (IIb) to a temperature of about −90° C., −80° C., −75° C., −70° C., −65° C., −60° C., −55° C., −50° C., −40° C., −30° C., −20° C., −10° C., or −5° C. prior to the combining of the continuous flow of the first reaction intermediate and the continuous flow of the compound of Formula (IIa) or (IIb). In some embodiments, the process described herein can further include pre-cooling the compound of Formula (IIa) or (IIb) to a temperature of about −60° C. prior to the combining of the continuous flow of the first reaction intermediate and the continuous flow of the compound of Formula (IIa) or (IIb). In some embodiments, the process described herein can further include pre-cooling the compound of Formula (IIa) or (IIb) to a temperature in the range of about −75° C. to −60° C. prior to the combining of the continuous flow of the first reaction intermediate and the continuous flow of the compound of Formula (IIa) or (IIb). In some embodiments, the process described herein can further include pre-cooling the compound of Formula (IIa) or (IIb) to a temperature in the range of about −80° C. to −65° C. prior to the combining of the continuous flow of the first reaction intermediate and the continuous flow of the compound of Formula (IIa) or (IIb). In some embodiments, the process described herein can further include pre-cooling the compound of Formula (IIa) or (IIb) to a temperature in the range of about −85° C. to −60° C. prior to the combining of the continuous flow of the first reaction intermediate and the continuous flow of the compound of Formula (IIa) or (IIb).

The process can further include pre-cooling the Lewis acid to a temperature suitable for the Matteson reaction. In some embodiments, the process described herein can further include pre-cooling the Lewis acid to a temperature of about −70° C., −60° C., −50° C., −40° C., −30° C., −25° C., −15° C., −10° C., −5° C., 0° C., or 10° C. prior to the treating. In some embodiments, the process described herein can further include pre-cooling the Lewis acid to a temperature of about −20° C. prior to the treating. In some embodiments, the process described herein can further include pre-cooling the Lewis acid to a temperature of about −25° C. prior to the treating. In some embodiments, the process described herein can further include pre-cooling the Lewis acid to a temperature of about −30° C. prior to the treating. In some embodiments, the process described herein can further include pre-cooling the Lewis acid to a temperature in the range of about −35° C. to about −25° C. prior to the treating. In some embodiments, the process described herein can further include pre-cooling the Lewis acid to a temperature in the range of about −25° C. to −20° C. prior to the treating. In some embodiments, the process described herein can further include maintaining the Lewis acid at a room temperature.

The process described herein can further include maintaining the first continuous flow conduit at a temperature in the range of about −100° C. to about 0° C. during the process. In some embodiments, the process described herein can further include maintaining the first continuous flow conduit at a temperature of about −85° C., −80° C., −75° C., −70° C., −65° C., −55° C., −50° C., or −45° C. In some embodiments, the process described herein can further include maintaining the first continuous flow conduit at a temperature of about −65° C., −64° C., −63° C., −62° C., or −61° C. In some embodiments, the process described herein can further include maintaining the first continuous flow conduit at a temperature of about −60° C. In some embodiments, the process described herein can further include maintaining the first continuous flow conduit at a temperature of about −75° C. In some embodiments, the process described herein can further include maintaining the first continuous flow conduit at a temperature in the range of about −75° C. to −60° C. In some embodiments, the process described herein can further include maintaining the first continuous flow conduit at a temperature in the range of about −80° C. to −65° C. In some embodiments, the process described herein can further include maintaining the first continuous flow conduit at a temperature in the range of about −85° C. to −60° C.

The process described herein can further include maintaining the second continuous flow conduit at a temperature in the range of about −100° C. to about 0° C. In some embodiments, the process described herein can further include maintaining the second continuous flow conduit at a temperature of about −80° C., −75° C., −70° C., −65° C., −55° C., −50° C., or −45° C. In some embodiments, the process described herein can further include maintaining the second continuous flow conduit at a temperature of about −65° C., −64° C., −63° C., −62° C., or −61° C. In some embodiments, the process described herein can further include maintaining the second continuous flow conduit at a temperature of about −60° C. In some embodiments, the process described herein can further include maintaining the second continuous flow conduit at a temperature of about −75° C. In some embodiments, the process described herein can further include maintaining the second continuous flow conduit at a temperature in the range of about −75° C. to −60° C. In some embodiments, the process described herein can further include maintaining the second continuous flow conduit at a temperature in the range of about −80° C. to −65° C. In some embodiments, the process described herein can further include maintaining the second continuous flow conduit at a temperature in the range of about −85° C. to −60° C.

The flow time in the continuous flow conduit can vary depending on the flow rate and the length of the continuous flow conduit. In some embodiments, a flow time from the input to the output of the first continuous flow conduit is about 5 second to about 50 seconds. In some embodiments, a flow time from the input to the output of the first continuous flow conduit is about 20, 21, 22, 23, 24, 25, 26, 27, 28, 29, or 30 seconds. In some embodiments, a flow time from the input to the output of the first continuous flow conduit is about 21 seconds. In some embodiments, a flow time from the input to the output of the second continuous flow conduit is about 5 seconds to about 50 seconds. In some embodiments, a flow time from the input to the output of the second continuous flow conduit is about 20, 21, 22, 23, 24, 25, 26, 27, 28, 29, or 30 seconds. In some embodiments, a flow time from the input to the output of the second continuous flow conduit is about 23 seconds.

In embodiments where dichloromethane is in a solvent (e.g., tetrahydrofuran), the concentration of the dichloromethane prior to flowing into the first continuous flow conduit in some embodiments is about 39%. In some embodiments, the concentration of the dichloromethane prior to flowing into the first continuous flow conduit is in the range of about 35% to about 45%. In some embodiments, the concentration of the dichloromethane prior to flowing into the first continuous flow conduit is in the range of about 30% to about 50%.

The molar ratio of alkyl lithium to dichloromethane can vary depending on the reaction temperature, the reaction solvent, and other reaction conditions in the continuous flow conduit. In some embodiments, the molar ratio of alkyl lithium to dichloromethane is in the range of about 1:1 to about 1:10. In some embodiments, the molar ratio of alkyl lithium to dichloromethane is about 1:3 to 1:4. In some embodiments, the molar ratio of alkyl lithium to dichloromethane is about 1.4:4.3. In some embodiments, the molar ratio of alkyl lithium to dichloromethane is about 1.2:4.3. In some embodiments, the molar ratio of alkyl lithium to dichloromethane is about 1.4:4.3 to about 1.2:4.3. In some embodiments, the molar ratio of alkyl lithium to dichloromethane is about 1:3. In some embodiments, the molar ratio of alkyl lithium to dichloromethane is in the range of about 1:5 to about 1:1.

In embodiments where a continuous flow of alkyl lithium is established prior to combination with tetrahydrofuran, the concentration of the alkyl lithium in the continuous flow prior to being combined with the tetrahydrofuran can vary depending on the reaction conditions. In some embodiments, the concentration of the alkyl lithium in the continuous flow prior to being combined with the tetrahydrofuran is about 25%. In some embodiments, the concentration of the alkyl lithium in the continuous flow prior to combination with the tetrahydrofuran is in the range of about 24% to about 26%. In some embodiments, the concentration of the alkyl lithium in the continuous flow prior to being combined with the tetrahydrofuran is in the range of about 15% to about 35%.

The concentration of the alkyl lithium in the continuous flow after being combined with the tetrahydrofuran but prior to flowing into the first continuous flow conduit can vary depending on the reaction conditions. In some embodiments, the concentration of the alkyl lithium in the continuous flow after being combined with the tetrahydrofuran but prior to flowing into the first continuous flow conduit is about 5.5%, 5.8%, 6.1%, 6.4%, or 6.7%. In some embodiments, the concentration of the alkyl lithium in the continuous flow after being combined with the tetrahydrofuran but prior to flowing into the first continuous flow conduit is in the range of about 5.5% to about 6.1%. In some embodiments, the concentration of the alkyl lithium in the continuous flow after being combined with the tetrahydrofuran but prior to flowing into the first continuous flow conduit is in the range of about 5.5% to about 6.4%. In some embodiments, the concentration of the alkyl lithium in the continuous flow after combination with the tetrahydrofuran but prior to flowing into the first continuous flow conduit is in the range of about 10% to about 2%.

The concentration of the compound of Formula (IIa) or (IIb) prior to flowing into the input of the second continuous flow conduit can vary depending on the reaction conditions. In some embodiments, the concentration of the compound of Formula (IIa) or (IIb) in a solvent prior to flowing into the input of the second continuous flow conduit is about 29%. In some embodiments, the concentration of the compound of Formula (IIa) or (IIb) prior to flowing into the input of the second continuous flow conduit is in the range of about 24% to about 33%. In some embodiments, the concentration of the compound of Formula (IIa) or (IIb) prior to flowing into the input of the second continuous flow conduit is in the range of about 15% to about 45%. In some embodiments, the concentration of the compound of Formula (IIa) or (IIb) prior to flowing into the input of the second continuous flow conduit is in the range of about 33% to about 43%. In some embodiments, the concentration of the compound of Formula (IIa) or (IIb) prior to flowing into the input of the second continuous flow conduit is in the range of about 25% to about 50%.

In embodiments wherein a compound of Formula (IIa) or (IIb) in heptane is established prior to combination with tetrahydrofuran, the concentration of the compound of Formula (IIa) or (IIb) in the heptane solution prior to combination with tetrahydrofuran is about 38%. In some embodiments, the concentration of the compound of Formula (IIa) or (IIb) in the heptane solution prior to combination with tetrahydrofuran is in the range of about 33% to about 43%. In some embodiments, the concentration of the compound of Formula (IIa) or (IIb) in the heptane solution prior to combination with tetrahydrofuran is in the range of about 25% to about 50%.

The molar ratio of alkyl lithium to the compound of Formula (IIa) or (IIb) can vary depending on the reaction temperature and other reaction conditions in the continuous flow conduit. In some embodiments, the molar ratio of alkyl lithium to the compound of Formula (IIa) or (IIb) is in the range of about 0.5:1 to about 5:1. In some embodiments, the molar ratio of alkyl lithium to the compound of Formula (IIa) or (IIb) is about 1:1 to 1.2:1. In some embodiments, the molar ratio of alkyl lithium to the compound of Formula (IIa) or (IIb) is about 1 to 1.16. In some embodiments, the molar ratio of alkyl lithium to the compound of Formula (IIa) or (IIb) is about 1.3. In some embodiments, the molar ratio of alkyl lithium to the compound of Formula (IIa) or (IIb) is in the range of about 1.5 to about 1.1. In some embodiments, the molar ratio of alkyl lithium to the compound of Formula (IIa) or (IIb) is bout 1.5, 1.4, 1.3, 1.2, 1.1, or 1. In some embodiments, the molar ratio of alkyl lithium to the compound of Formula (IIa) or (IIb) is in the range of about 0.5 to about 2.

The molar ratio of Lewis acid to the compound of Formula (IIa) or (IIb) can vary depending on the reaction temperature and other reaction conditions in the continuous flow conduit. In some embodiments, the molar ratio of Lewis acid to the compound of Formula (IIa) or (IIb) is higher than about 3, 4, 5, 6, 7, 8, or 10. In some embodiments, the molar ratio of Lewis acid to the compound of Formula (IIa) or (IIb) is higher than about 2. In some embodiments, the molar ratio of Lewis acid to the compound of Formula (IIa) or (IIb) is in the range of about 0.5:1 to about 5:1. In some embodiments, the molar ratio of Lewis acid to the compound of Formula (IIa) or (IIb) is about 1:1 to 1.5:1. In some embodiments, the molar ratio of Lewis acid to the compound of Formula (IIa) or (IIb) is about 3.0, 2.9. 2.8, 2.7, 2.6, 2.5, 2.4, 2.3, 2.2, 2.1, or 2.0. In some embodiments, the molar ratio of Lewis acid to the compound of Formula (IIa) or (IIb) is in the range of about 2.0 to 2.5. In some embodiments, the molar ratio of Lewis acid to the compound of Formula (IIa) or (IIb) is in the range of about 1.0 to 5.0.

The concentration of Lewis acid in the vessel prior to reacting with the second reaction intermediate that flows out the output of the third continuous flow conduit may vary depending on the reaction condition. In some embodiments, the concentration of Lewis acid in the vessel prior to reacting with the second reaction intermediate that flows out the output of the third continuous flow conduit is about 11.8%. In some embodiments, the concentration of Lewis acid in the vessel prior to reacting with the second reaction intermediate that flows out the output of the third continuous flow conduit is in the range of about 8% to about 15%. In some embodiments, the concentration of Lewis acid in the vessel prior to reacting with the second reaction intermediate that flows out the output of the third continuous flow conduit is in the range of about 5% to about 20%.

When the Lewis acid is a zinc chloride, the amount of zinc chloride in the vessel before reaction with the second reaction intermediate can be calculated based on the amount of the compound of formula (IIa) or (IIb) added in the process. For example, 0.70 kg of Zinc chloride can be added for every kilogram of the compound of the formula (IIa) or (IIb). In some embodiments, the amount of Zinc chloride added for every kilogram of the compound of the formula (IIa) or (IIb) is in the range of about 0.5 kg to about 1 kg. In some embodiments, the amount of Zinc chloride added for every kilogram of the compound of the formula (IIa) or (IIb) is in the range of about 0.2 kg to about 1.5 kg.

The flow rate of alkyl lithium in the first continuous flow conduit may vary depending on the reaction conditions. The process described herein can include flowing the alkyl lithium into the first continuous flow conduit at a flow rate of about 2.0 mmol/min, 4.0 mmol/min, 6.0 mmol/min, 8.0 mmol/min, 10.0 mmol/min, 12.0 mmol/min, or 15.0 mmol/min. In some embodiments, the process described herein can further include flowing the alkyl lithium into the first continuous flow conduit at a flow rate of about 0.1 mmol/min to about 5.0 mmol/min. In some embodiments, the alkyl lithium flow rate is about 0.8 mmol/min to about 1.2 mmol/min, or about 0.8 mmol/min to about 2.7 mmol/min. In some embodiments, the alkyl lithium flow rate is about 0.9 mmol/min. In some embodiments, the alkyl lithium flow rate is 8.4 mol/h. In some embodiments, the alkyl lithium flow rate is in the range of about 8.0 mol/h to about 8.7 mol/h. In some embodiments, the alkyl lithium flow rate is in the range of about 5.0 mol/h to about 10.0 mol/h.

The flow rate of dichloromethane in the first continuous flow conduit may vary depending on the reaction conditions. The process described herein can include flowing dichloromethane into the first continuous flow conduit at a flow rate of about 2.0 mmol/min, 4.0 mmol/min, 6.0 mmol/min, 8.0 mmol/min, 10.0 mmol/min, 12.0 mmol/min, or 15.0 mmol/min. The process described herein can further include flowing the dichloromethane into the first continuous flow conduit at a flow rate of about 1 mmol/min to about 5 mmol/min. In some embodiments, the dichloromethane flow rate is about 2.5 mmol/min to about 3.0 mmol/min. In some embodiments, the dichloromethane flow rate is about 2.8 mmol/min. The process described herein can further include flowing the dichloromethane into the first continuous flow conduit at a flow rate of about 200 mmol/min to about 700 mmol/min. The process described herein can further include flowing the dichloromethane into the first continuous flow conduit at a flow rate of about 300 mmol/min to about 600 mmol/min. The process described herein can further include flowing the dichloromethane into the first continuous flow conduit at a flow rate of about 400 mmol/min to about 500 mmol/min. The process described herein can further include flowing the dichloromethane into the first continuous flow conduit at a flow rate of about 420 mmol/min to about 450 mmol/min. The process described herein can further include flowing the dichloromethane into the first continuous flow conduit at a flow rate of about 433 mmol/min.

The flow rate of the compound of Formula (IIa) or (IIb) in the second continuous flow conduit may vary depending on the reaction conditions. The process described herein can include flowing the compound of Formula (IIa) or (IIb) into the second continuous flow conduit at a flow rate of about 0.1 mmol/min to about 5 mmol/min. In some embodiments, the flow rate of the compound of Formula (IIa) or (IIb) is about 0.5 mmol/min to about 1.0 mmol/min. In some embodiments, the flow rate of the compound of Formula (IIa) or (IIb) is about 0.668 mmol/min. In some embodiments, the flow rate of the compound of Formula (IIa) or (IIb) is about 6.4 mol/h. In some embodiments, the flow rate of the compound of Formula (IIa) or (IIb) is in the range of about 5.6 mol/h to about 7.2 mol/h. In some embodiments, the flow rate of the compound of Formula (IIa) or (IIb) is in the range of about 2.0 mol/h to about 10.0 mol/h.

In some embodiments, the treating of the second reaction intermediate with the Lewis acid is not performed in a continuous flow conduit. In some embodiments, the treating of the second reaction intermediate with the Lewis acid is performed in a flask or other reaction vessel that does not involve continuous flowing of Lewis acid solution.

In some embodiments, the treating of the second reaction intermediate with the Lewis acid is performed in a continuous flow conduit. In some embodiments, the treating of the second reaction intermediate with the Lewis acid is performed in a vessel containing at least one continuous flow conduit.

The process described herein can also include one or more steps known by those skilled in the art to be suitable for separating and purifying the compound of formula (Ia) or (Ib). The separation and/or purification can include extraction, distillation, chromatography and other suitable purifying methods known by those skilled in the art. For example, the separation and/or purification can include multiple extraction steps using the same or different solvents in each extraction step, and one or more distillation steps can be used following the extraction to further purify the final product.

The process described herein can further include one or more steps of preparing stock solution of the various reagents. In some embodiments, the process described herein can further include combining alkyl lithium in heptane and tetrahydrofuran to prepare an alkyl lithium stock solution for the first continuous flow of alkyl lithium. In an embodiment wherein the continuous flow of tetrahydrofuran and the continuous flow of alkyl lithium are provided separately, the process described herein can further include combining alkyl lithium and heptane to prepare an alkyl lithium in heptane stock solution for the separate continuous flow of alkyl lithium. In some embodiments, the process described herein can further include combining dichloromethane and tetrahydrofuran to provide a dichloromethane stock solution for the continuous flow of dichloromethane. In some embodiments, the process described herein can further include combining the compound of Formula (IIa) or (IIb) and heptane to provide a compound of Formula (IIa) or (IIb) stock solution for the continuous flow of the compound of Formula (IIa) or (IIb). In some embodiments, the process described herein can further include combining the compound of Formula (IIa) or (IIb) and tetrahydrofuran to provide a compound of Formula (IIa) or (IIb) stock solution for the continuous flow of the compound of Formula (IIa) or (IIb). In some embodiments, the process described herein can further include combining the compound of Formula (IIa) or (IIb), tetrahydrofuran, and heptane to provide a compound of Formula (IIa) or (IIb) stock solution for the continuous flow of the compound of Formula (IIa) or (IIb). In some embodiments, the process described herein can further include combining a Lewis acid and tetrahydrofuran to provide a Lewis acid stock solution for the Lewis acid. The stock solution can be prepared in a continuous flow conduit.

The process described herein can also include pressurizing the vessel containing the stock solutions. In some embodiments, the process described herein includes pressurizing the fifth vessel comprising the alkyl lithium stock solution. In some embodiments, the process described herein includes pressurizing the sixth vessel comprising the dichloromethane stock solution. In some embodiments, the process described herein includes pressurizing the seventh vessel comprising the compound of Formula (IIa) or (IIb). In some embodiments, the process described herein includes pressurizing a vessel comprising the Lewis acid stock solution. In an embodiment wherein the continuous flow of tetrahydrofuran and the continuous flow of alkyl lithium are provided separately, the process described herein can further include preparing a stock solution of alkyl lithium in heptane and pressurizing a vessel comprising the alkyl lithium in heptane stock solution. In such an embodiments, the process described herein can further include preparing a stock solution of tetrahydrofuran and pressurizing a vessel comprising the tetrahydrofuran stock solution.

In some embodiments, the alkyl lithium is n-butyl lithium.

In some embodiments, the Lewis acid is zinc chloride. In some embodiments, the Lewis acid is boron trifluoride. In some embodiments, the Lewis acid is aluminum chloride. In some embodiments, the Lewis acid is magnesium chloride.

In some embodiments, the process includes producing the compound of Formula Ia. In some embodiments, for the compound of Formula (Ia), M is —CH═CH— and n is 1. In some embodiments, for the compound of Formula (Ia), M is —CH$_2$— and Q is —CH$_2$— or —CH$_2$—CH$_2$—.

In some embodiments, the process includes producing the compound of Formula Ib. In some embodiments, the compound of Formula Ib has a structure of formula III

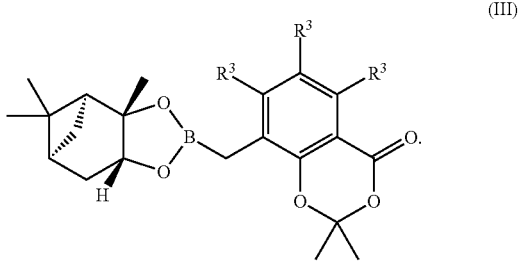

In some embodiments, $R^1$ is tert-butyldimethylsilyl (TBDMS).

In some embodiments, $R^2$ is tert-butyl (t-Bu).

In some embodiments, the compound of Formula Ia is

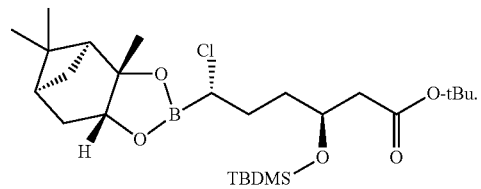

In some embodiments, the compound of Formula (IIa) is

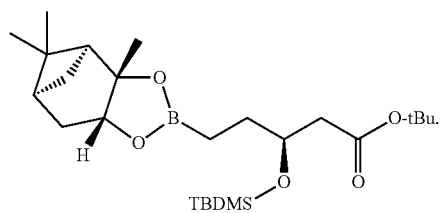

The process described herein can further include performing the collecting and treating under a nitrogen or argon atmosphere.

The process described herein can be used for production of the compound of formula (Ia) or (Ib) on a plant scale or pilot plant scale. The process described herein can be used to produce over about 10 kg, 20 kg, 50 kg, 80 kg, 100 kg, 150 kg, 180 kg, or 200 kg of the compound of formula (Ia) or (Ib) per day.

Apparatus for a Continuous Production Process

FIG. 1 is a non-limiting schematic of an apparatus for a continuous production process as described herein. FIG. 1 shows an apparatus 050 for production of a compound of Formula Ia or Ib,

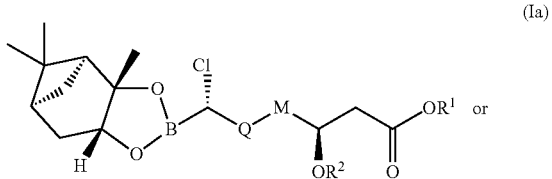

-continued (Ib)

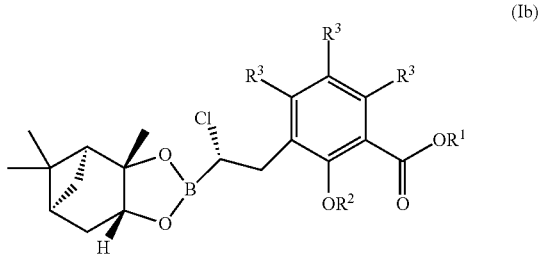

wherein the apparatus 050 includes:
a first vessel 004 having an output and comprising alkyl lithium;
a second vessel 005 having an output and comprising dichloromethane;
a first continuous flow conduit 002 comprising an input and an output, wherein the input of the first continuous flow conduit is fluidly coupled to the output of the first vessel 004 and the output of the second vessel 005;
a third vessel 007 having an output and comprising a compound of Formula (IIa) or (IIb);

(IIa)

or (IIb)

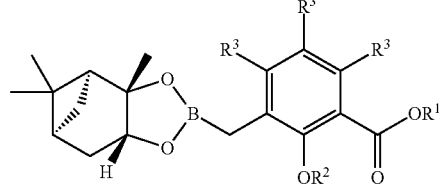

a second continuous conduit 003 comprising an input and an output, wherein the input of the second continuous conduit is fluidly coupled to the output of the first continuous flow conduit and the output of the third vessel 007;
a fourth vessel 010 having an input fluidly coupled to the output of the second continuous flow conduit and comprising Lewis acid.

The apparatus described herein can include one or more vessels containing the stock solutions of one or more reagents. In some embodiments, the apparatus described herein can further include a fifth vessel fluidly coupled to the first vessel, wherein the fifth vessel comprises a stock solution of alkyl lithium in hexane and tetrahydrofuran. In some embodiments, the apparatus described herein can further include a sixth vessel fluidly coupled to the second vessel, wherein the sixth vessel comprises a stock solution of dichloromethane in tetrahydrofuran. In some embodiments, the apparatus described herein can further include a seventh vessel fluidly coupled to the third vessel, wherein the seventh vessel comprises a stock solution of the compound of Formula (IIa) or (IIb) in heptane.

One or more flow control members can be used in the apparatus to control the flow rate. The apparatus described herein can further include one or more flow control members fluidly coupled to the vessels comprising stock solutions of alkyl lithium, tetrahydrofuran, dichloromethane, or the compound of formula (IIa) or (IIb). The flow control members can be a pneumatic flow control including but not limited to a pressurized vessel; a valve; any pump known to be suitable for flow control, including but not limited to a syringe pump; any other flow control equipment known in the art; and combinations thereof.

The vessel containing a stock solution can be pressurized depending on the flow control member used in the apparatus. In an embodiment wherein a valve is used to control the flow rate, a pressurized vessel containing a stock solution instead of a pump can be used in the apparatus described herein. In some embodiments, the fifth vessel which comprises a stock solution of alkyl lithium can be pressurized. In some embodiments, the six vessel which comprises a stock solution of dichloromethane can be pressurized. In some embodiments, the seventh vessel which comprises a stock solution of the compound of Formula (IIa) or (IIb) can be pressurized.

As shown in FIG. 1, the output of the alkyl lithium stock solution vessel 004 is fluidly coupled to the input of the third continuous flow conduit 001 through a valve 004a. The output of the dichloromethane stock solution vessel 005 is fluidly coupled to the input of the continuous flow conduit 006 through a valve 005a. The output of the compound (IIa) or (IIb) stock solution vessel 007 is fluidly coupled to the input of the continuous flow conduit 008 through a valve 007a.

One or more vessels in the apparatus can be a continuous flow conduit. In some embodiments, the first vessel includes a third continuous flow conduit 001 having an input and an output, wherein the output of the third continuous flow conduit 001 is fluidly coupled with the input of the first continuous flow conduit 002. In some embodiments, the second vessel includes a continuous flow conduit 006. In some embodiments, the third vessel includes a continuous flow conduit 008.

In some embodiments, the fourth vessel includes a continuous flow conduit. In some embodiments, the fourth vessel does not have a continuous flow conduit.

In some embodiments, the fifth vessel includes a continuous flow conduit. In some embodiments, the fifth vessel is fluidly coupled to the first vessel and the fifth vessel comprises a stock solution of alkyl lithium. In some embodiments, the sixth vessel includes a continuous flow conduit. In some embodiments, the sixth vessel is fluidly coupled to the second vessel and the sixth vessel comprises a stock solution of dichloromethane. In some embodiments, the seventh vessel includes a continuous flow conduit. In some embodiments, the seventh vessel is fluidly coupled to the third vessel and the seventh vessel comprises a stock solution of the compound of Formula (IIa) or Formula (IIb).

In some embodiments, the first vessel comprises:
a fourth continuous flow conduit having an input and an output, wherein the output of the fourth continuous fluid conduit is fluidly coupled to the input of the third continuous flow conduit, wherein the fourth continuous flow conduit comprises alkyl lithium; and
a fifth continuous flow conduit having an input and an output, wherein the output of the fifth continuous flow conduit is fluidly coupled to the input of the third continuous flow conduit, wherein the fifth continuous flow conduit comprises tetrahydrofuran.

In some embodiments, the apparatus described herein can further comprise:
- an alkyl lithium vessel fluidly coupled with the input of the fourth continuous flow conduit, wherein the alkyl lithium vessel comprises a stock solution of alkyl lithium in heptane; and
- a tetrahydrofuran vessel fluidly coupled to the input of the fifth continuous flow conduit, wherein the tetrahydrofuran vessel comprises a stock solution of tetrahydrofuran.

In some embodiments, the alkyl lithium vessel and the tetrahydrofuran vessel are pressurized.

The apparatus described herein can further include one or more cooling elements thermally coupled to at least one of the first continuous flow conduit 002 and the second continuous flow conduit 003. The apparatus described herein can further include one or more cooling elements thermally coupled to at least one of the third, the fourth, and the fifth continuous flow conduit. The apparatus described herein can further include one or more cooling elements thermally coupled to at least one of the first, the second, and the third vessels. The apparatus described herein can further include a cooling element thermally coupled to the fourth vessel. The apparatus described herein can further include a cooling element thermally coupled to the fifth, sixth, and seventh vessel. In an embodiment that a continuous flow of tetrahydrofuran is provided separately from a continuous flow of alkyl lithium in heptane before the two flows are combined, the apparatus described herein can further include a cooling element thermally coupled to the alkyl lithium in heptane stock solution vessel and the tetrahydrofuran stock solution vessel.

The cooling element can be any suitable cooling equipment known in the art. In some embodiments, the cooling element comprises a cooling bath 009. In some embodiments, the cooling element comprises a mixture of dry ice and acetone. The cooling element can be any suitable cooling methods known by those skilled in the art.

The apparatus described herein can further include a gas purging member configured to purge the apparatus with nitrogen or argon atmosphere.

The continuous flow conduit can be made of any suitable materials known in the art for conducting chemical reactions performed under low temperatures. In some embodiments, the continuous flow conduit can be made of stainless steel. In some embodiments, the first and second continuous flow conduits are made of stainless steel. In some embodiments, the first, the second, and the third vessels are made of stainless steel.

In some embodiments, the fourth vessel 010 is not a continuous flow conduit. In some embodiments, the fourth vessel 010 can be a flask or a reaction vessel that does not involve the reaction mixture flowing out of the flask or reaction vessel.

The dimension of the first continuous flow conduit can vary depending on the reaction conditions and the production scale. In some embodiments, the first continuous flow conduit is made of a tubing having a length in the range of about 0.1 m to about 10 m. In some embodiments, the first continuous flow conduit is made of a tubing having a length of about 1.42 m. In some embodiments, the first continuous flow conduit is made of a spiral tubing having a volume in the range of about 0.1 ml to about 100 ml. In some embodiments, the first continuous flow conduit is made of a spiral tubing having a volume of about 1.12 ml.

In some embodiments, the second continuous flow conduit is made of a tubing having a length in the range of about 0.1 m to about 10 m. In some embodiments, the second continuous flow conduit is made of a tubing having a length of about 3.15 m. In some embodiments, the second continuous flow conduit is made of a tubing having a volume in the range of about 0.1 ml to about 100 ml. In some embodiments, the second continuous flow conduit is made of a tubing having a volume of about 2.5 ml. The tubing can be of straight or spiral.

In some embodiments, the fourth continuous flow conduit for delivering the alkyl lithium to the input of the third continuous flow conduit is made of a tubing having a length of about 0.1 m to about 10 m. In some embodiments, the fourth continuous flow conduit for delivering the alkyl lithium to the input of the third continuous flow conduit is made of a tubing having a length in the range of about 0.1 m to about 10 m. In some embodiments, the fifth continuous flow conduit for delivering the tetrahydrofuran to the input of the third continuous flow conduit is made of a tubing having a length of about 0.1 m to about 10 m. In some embodiments, the fifth continuous flow conduit for delivering the tetrahydrofuran to the input of the third continuous flow conduit is made of a tubing having a length in the range of about 0.1 m to about 10 m.

In some embodiments, the continuous flow conduit for delivering dichloromethane to the input of the first continuous flow conduit is made of a tubing having a length of about 0.1 m to 10 m. In some embodiments, the continuous flow conduit for delivering dichloromethane to the input of the first continuous flow conduit is made of a tubing having a length in the range of about 0.2 m to about 10 m. In some embodiments, the continuous flow conduit for delivering the compound of Formula (IIa) or (IIb) to the input of the second continuous flow conduit is made of a tubing having a length of about 0.5 m to about 10 m. In some embodiments, the continuous flow conduit for delivering the compound of Formula (IIa) or (IIb) to the input of the second continuous flow conduit is made of a tubing having a length in the range of about 0.5 m to about 10 m.

The apparatus described herein can further include one or more flow control members fluidly coupled to the first, the second, the third, the fourth, the fifth, the sixth, or the seventh vessel. In some embodiments, the flow control member is fluidly coupled to the input of the first, the second, or the third vessel. In some embodiments, the flow control member is fluidly coupled to the output of the first, the second, or the third vessel. In some embodiments, the flow control member is fluidly coupled to at least one of the first, the second, and the third vessels. In some embodiments, the flow control member is fluidly coupled to the output of the fifth, sixth, or seventh vessel. In some embodiments, the flow control member is fluidly coupled to the input of the fourth vessel.

In some embodiments, the apparatus here is used for the production of the compound of Formula (Ia). In some embodiments, the apparatus here is used for the production of the compound of Formula (Ib). In some embodiments, the third vessel includes the compound of Formula (IIa). In some embodiments, the third vessel includes the compound of Formula (IIb).

The apparatus described herein can be used for production of the compound of formula (Ia) or (Ib) on a plant scale. The apparatus described herein can be used to produce more than about 10 kg, 100 kg, 250 kg, 500 kg, 800 kg of the compound of formula (Ia) or (Ib) per day.

The following examples will further describe the present invention, and are used for the purposes of illustration only, and should not be considered as limiting.

EXAMPLES

Comparative Example 1

The Matteson reaction described in scheme 1 was performed in a batch experiment. To a solution of dichloromethane in THF at −100° C. was added 2.5 M n-butyl lithium in hexane slowly under nitrogen and down the inside wall of the flask whilst maintaining the temperature below −90° C. The resulting white precipitate was stirred for 30 minutes before the addition of compound 1 in THF at −90° C. Zinc chloride was then added to the reaction mixture at −90° C. and then the reaction was allowed to warm to room temperature where it was stirred for 16 h. The reaction was quenched with a saturated solution of ammonium chloride and the phases were separated. The aqueous phase was then extracted with diethyl ether and the combined organic extracts were dried over $Na_2SO_4$, filtered and concentrated under reduced pressure. The concentrated material was then chromatographed purified to obtain the compound A. The batch reaction resulted in 75% yield. The obtained product was used as reference material in setting up the analytical method needed for monitoring the reaction in the other examples.

Example 1

Figure 2:
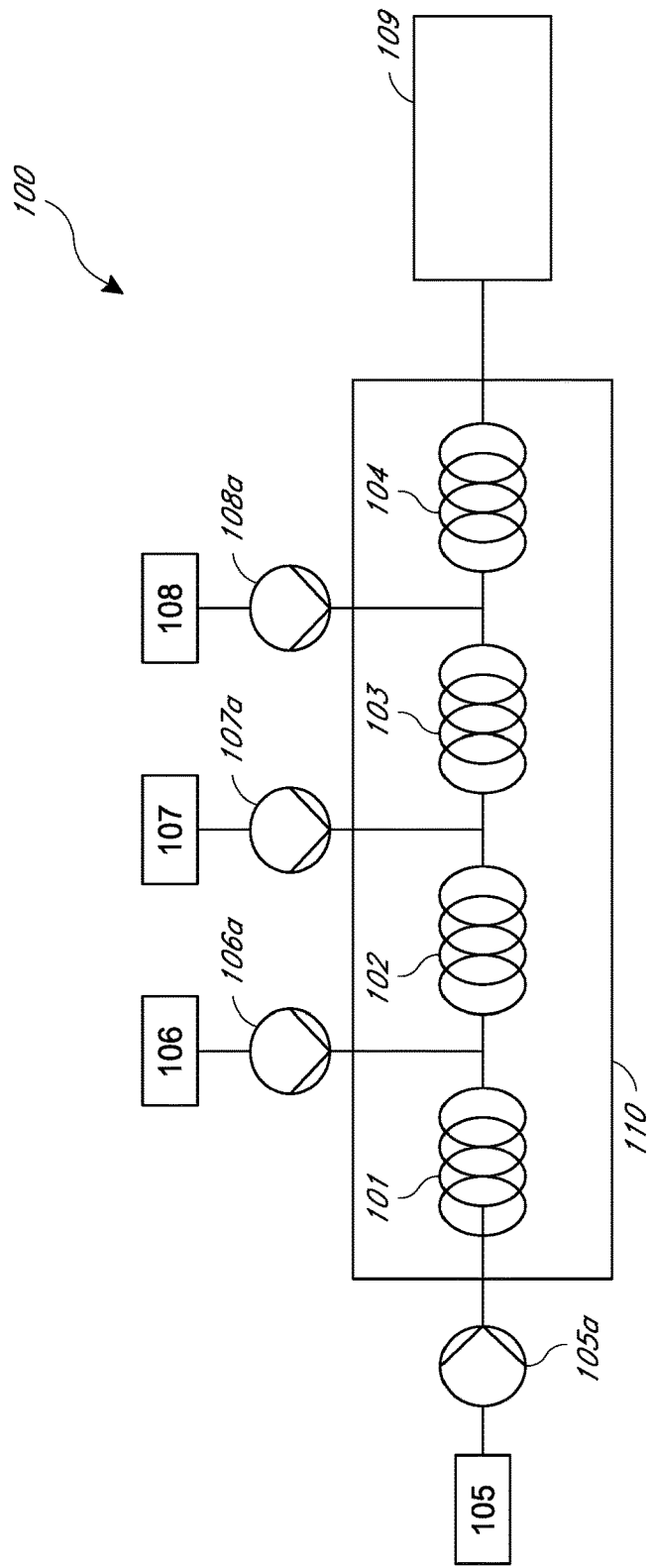
FIG. 2 is a schematic of the continuous flow process used in Example 1.

The experimental set-up 100 as schematically outlined in FIG. 2 was used. As shown in FIG. 2, a continuous flow conduit 101 is used for delivering the n-butyl lithium solution (in hexane), a continuous flow conduit 102 is used for mixing the n-butyl lithium and dichloromethane reagents and for delivering the reaction mixture to the next step, a continuous flow conduit 103 is used for combining the compound of Formula (IIa) or (IIb) and the reaction mixture that flows out of the continuous flow conduit 102, and a continuous flow conduit 104 is used for combining zinc chloride and the reaction mixture that flows out of the continuous flow conduit 103. During the reaction process, the n-butyl lithium stock solution in hexane was continuously added into the reaction process from the n-butyl lithium stock solution vessel 105 through a valve 105a and the n-butyl lithium was cooled in the continuous flow conduit 101 by using a cooling bath 110; a dichloromethane stock solution in THF was continuously added into the reaction process from the dichloromethane stock solution vessel 106 through a valve 106a; the mixture of n-butyl lithium and dichloromethane continuously flowed through the continuous flow conduit 102, which was cooled in the cooling bath 110; the stock solution of compound 1 was continuously added into the reaction process from the compound 1 stock solution vessel 107 through a valve 107a and was later combined with the reaction mixture that flowed out of the continuous flow conduit 102 in the continuous flow conduit 103, which was cooled in the cooling bath 110; the zinc chloride stock solution in THF was continuously added into the reaction process from the zinc chloride stock solution vessel 108 through a valve 108a and was later combined with the reaction mixture that flowed out the continuous flow conduit 103 in the continuous flow conduit 104; and the reaction mixture that flowed out of the continuous flow conduit 104 was then collected in a collection vessel 109. The continuous flow conduit 104, in which the zinc chloride was introduced and combined with the reaction mixture from the continuous flow conduit 103, was kept outside of the cooling bath 110 and maintained at an ambient temperature. As illustrated in FIG. 2, a valve such as 105a, 106a, 107a, or 108a can be used to fluidly couple an output of a vessel to input of a continuous flow conduit.

In this experiment, 1.6 M of n-butyl lithium stock solution in hexane, 17% of dichloromethane stock solution in THF, 0.6 M of the compound 1 stock solution in THF rather than n-heptane, and 0.5 M of zinc chloride stock solution in THF were prepared and used in the continuous flow process. The starting materials were kept under nitrogen atmosphere and dry solvents (with Karl Fischer reagent showing the amount of water <0.01%) were used to prepare the stock solutions.

The continuous flow set-up used here was made of stainless steel and was built using 1/16″ spiraled tubing (internal diameter: 1 mm). The system was controlled using four Gilson 307 HPLC pumps, temperature control was achieved using a cooling bath with different media to maintain the desired reaction temperature.

The n-butyl lithium solution was sufficiently cooled down through the continuous flow conduit 101 prior to reacting with dichloromethane. The cooled BuLi reacted with dichloromethane in the continuous flow conduit 102. The obtained lithium species subsequently reacted with the substrate compound 1 in the continuous flow conduit 103 to form a second intermediate which was than rearranged upon contact with $ZnCl_2$ in the continuous flow conduit 104. The product leaving the reaction mixture produced in the continuous flow conduit 104 was collected under nitrogen atmosphere, quenched with a 1N HCl solution and analyzed for the amount of Compound A.

Two parameters were adjusted in the continuous flow reaction described here, including the reaction temperature and residence time. The temperatures was adjusted by changing the composition of the dry ice and acetone mixture in the cooling bath 110, the residence time in each continuous flow conduit was increased or decreased by adjusting the length of the continuous flow conduits 101, 102, 103, and 104. The results obtained are summarized in table 1.

TABLE 1

Experimental results of continuous flow Matteson reaction in Example 1.

| Experiment # | Temperature (° C.) | | Residence Time (s) | | | | HPLC (area %) | |
|---|---|---|---|---|---|---|---|---|
| | 101-103 | 104 | 101 | 102 | 103 | 104 | Cmpd 1 | Cmpd A |
| 1.1 | −40 | 20 | 20 | 10 | 10 | 10 | 82 | 18 |
| 1.2 | −78 | 20 | 20 | 10 | 10 | 10 | 55 | 45 |
| 2.1 | −78 | 20 | 20 | 20 | 10 | 10 | 20 | 80 |
| 2.2 | −78 | 20 | 20 | 20 | 20 | 10 | 10 | 90 |
| 3.1 | −40 | 20 | 20 | 20 | 10 | 10 | 90 | 10 |
| 3.2 | −40 | 20 | 20 | 20 | 20 | 10 | 90 | 10 |

Figure 3A:
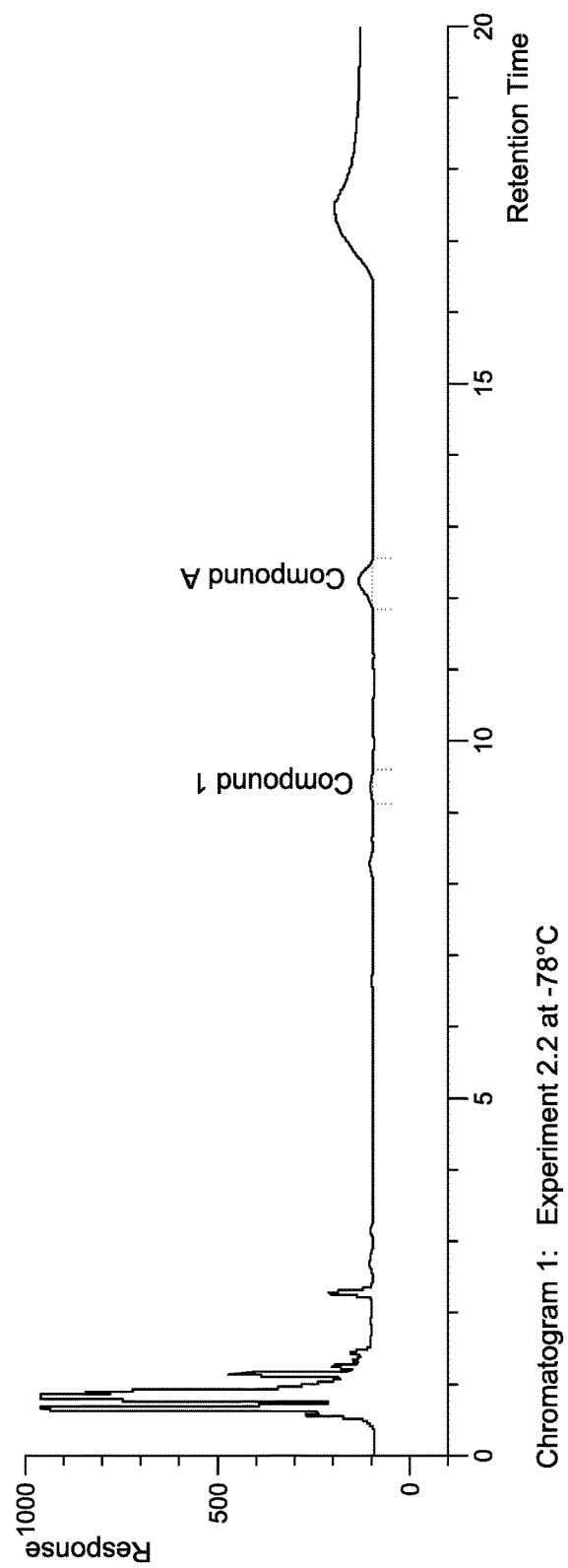
FIGS. 3A and 3B show the HPLC traces of the experiments 2.2 and 3.2 listed in Table 1.
Figure 3B:
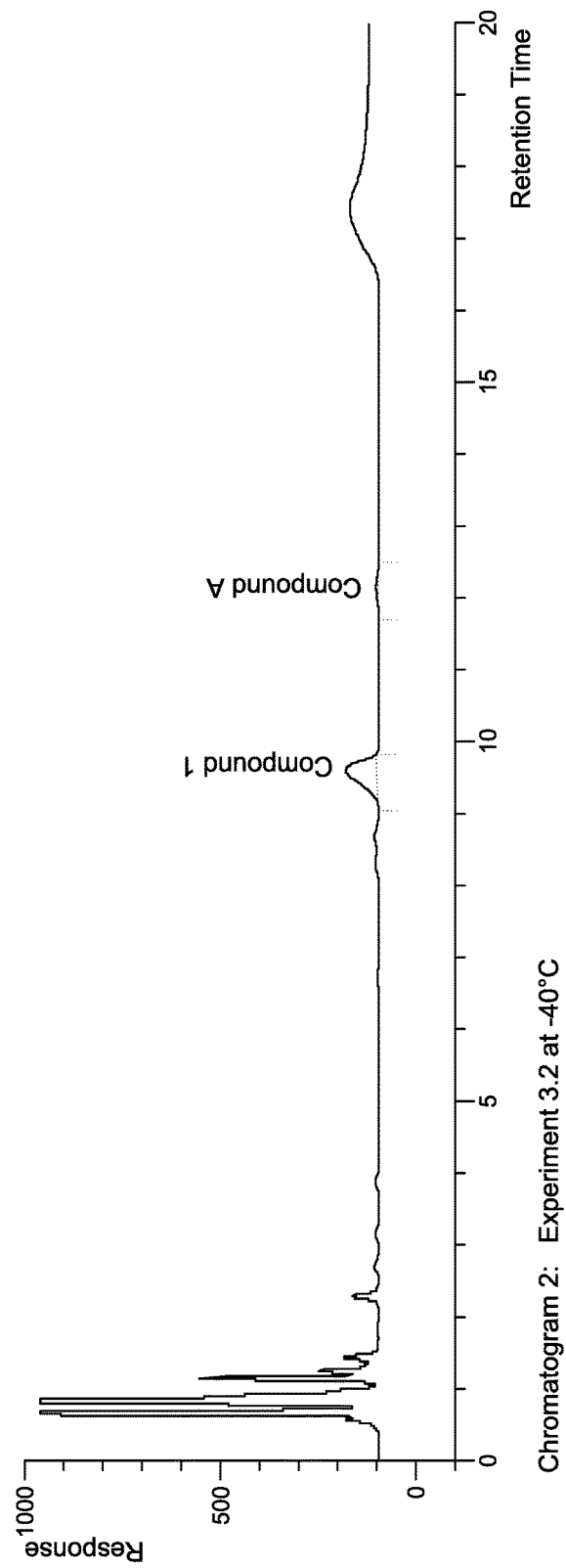

FIGS. 3A and 3B show the HPLC traces of the reaction mixture collected in experiments 2.2 and 3.2 respectively. In Experiment 2.2, the continuous flow conduits 101 to 103 were cooled to −78° C., while the continuous flow conduit 104 was maintained at 20° C. Experiment 2.2 showed the highest conversion rate of 90% based on the calculation of the areas for compound 1 and compound A in the HPLC chart. In Experiment 3.2, the continuous flow conduits 101 to 103 were cooled to −40° C., while the continuous flow conduit 104 was maintained at 20° C. Experiment 3.2 showed a conversion rate of 10% based on the calculation of the areas for compound 1 and compound A in the HPLC chart. In addition, the HPLC chart of experiment 3.2 shows more impurities than that of experiment 2.2.

The experiments listed in Table 1 indicated that longer residence time in the continuous flow conduits 102 and 103 may result in an increase conversion rate. However, additional experiments which increased the residence time from 20 seconds to 30 seconds only provided 40% conversion of compound 1. This was explained by the possibility that the particular residence time in the continuous flow conduit 102 was too long and may have resulted in the decomposition of the lithium-dichloromethane species that was formed in the continuous flow conduit 102. However, when the residence time in the continuous flow conduits 102 and 103 was reduced again to 20 seconds, the results of experiment 2.2 could not be reproduced and only 50% conversion of the compound 1 was achieved. It was also noted that the product stream coming out of the flow conduit was significantly less colored than before, which suggested that the Li-dichloromethane species was not properly being formed. Therefore, the experimental set-up used here did not produce consistent reaction results and had poor reproducibility and low conversion rates.

Example 2

Figure 4:
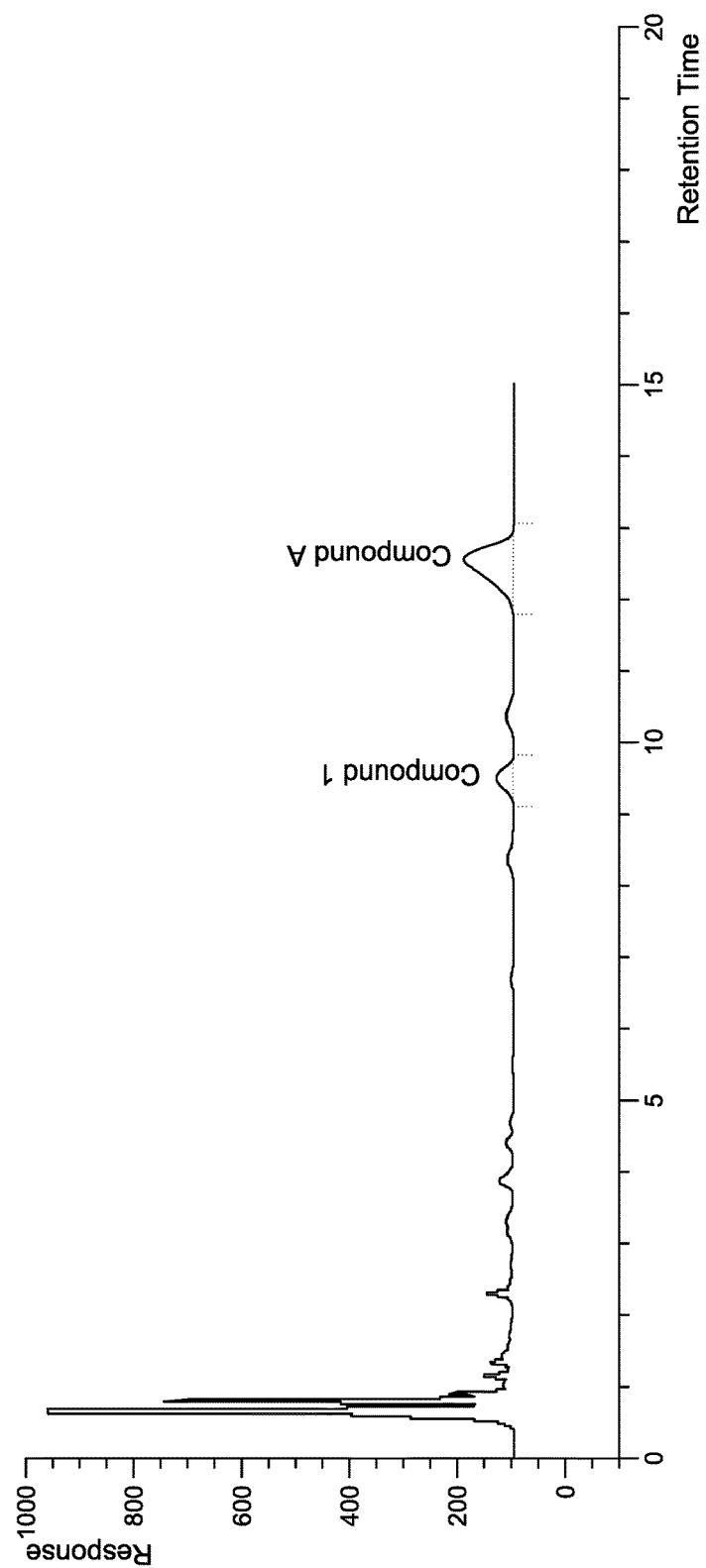
FIG. 4 shows the HPLC trace of reaction mixture after addition of second portion of LiCH$_2$Cl in the Example 1.

The experimental set-up as schematically outlined in FIG. 2 was used except that a second portion (dual injection) of the BuLi/dichloromethane mixture was added to the reaction mixture that flowed out of the continuous flow conduit 103. As shown in FIG. 4, the HPLC trace of the reaction mixture collected after addition of the second portion of BuLi/dichloromethane mixture shows that the ratio of compound 1 to compound A was 84:16.

Example 3

Figure 5:
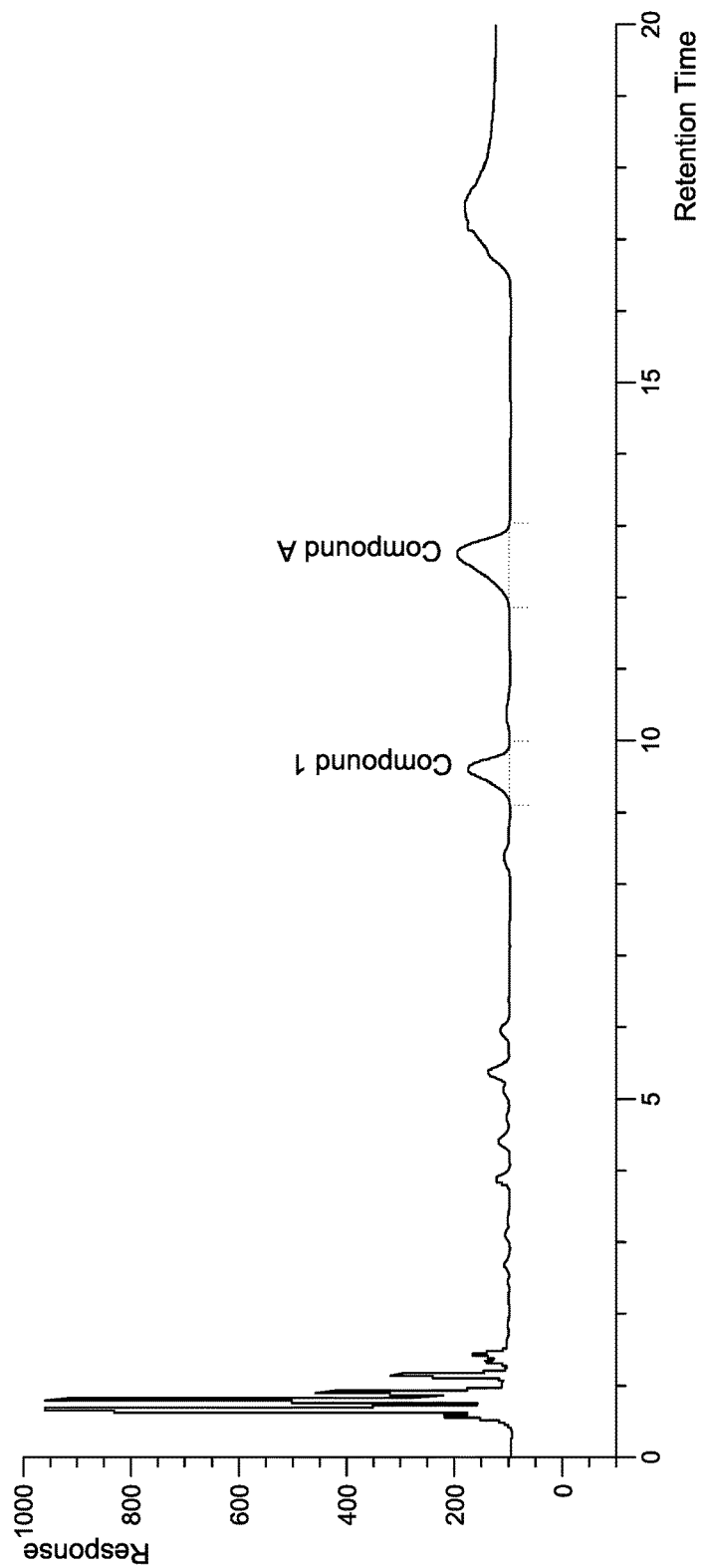
FIG. 5 shows the HPLC trace of Matteson reaction without addition of ZnCl$_2$.

The experimental set-up as schematically outlined in FIG. 2 was used except that a second portion (dual injection) of the BuLi/dichloromethane mixture was added to the reaction mixture that flowed out of the continuous flow conduit 103 but no zinc chloride was added. FIG. 5 shows the HPLC analysis of the reaction mixture collected from this reaction process, and the ratio of compound 1 to compound A was about 66:34 and the level of impurities was high.

Example 4

The n-butyl lithium stock solution in hexane was diluted with THF to prevent precipitation at low temperatures. This stock solution was prepared and kept at −78° C. The dichloromethane/THF solution and Compound 1 in heptane solution were pre-cooled to −15° C. In order to avoid precipitation the $ZnCl_2$ solution was not pre-cooled. All other stock solutions were cooled prior to entering the pump, and then cooled again using a cooling spiral residing in the cooling bath.

Figure 6:
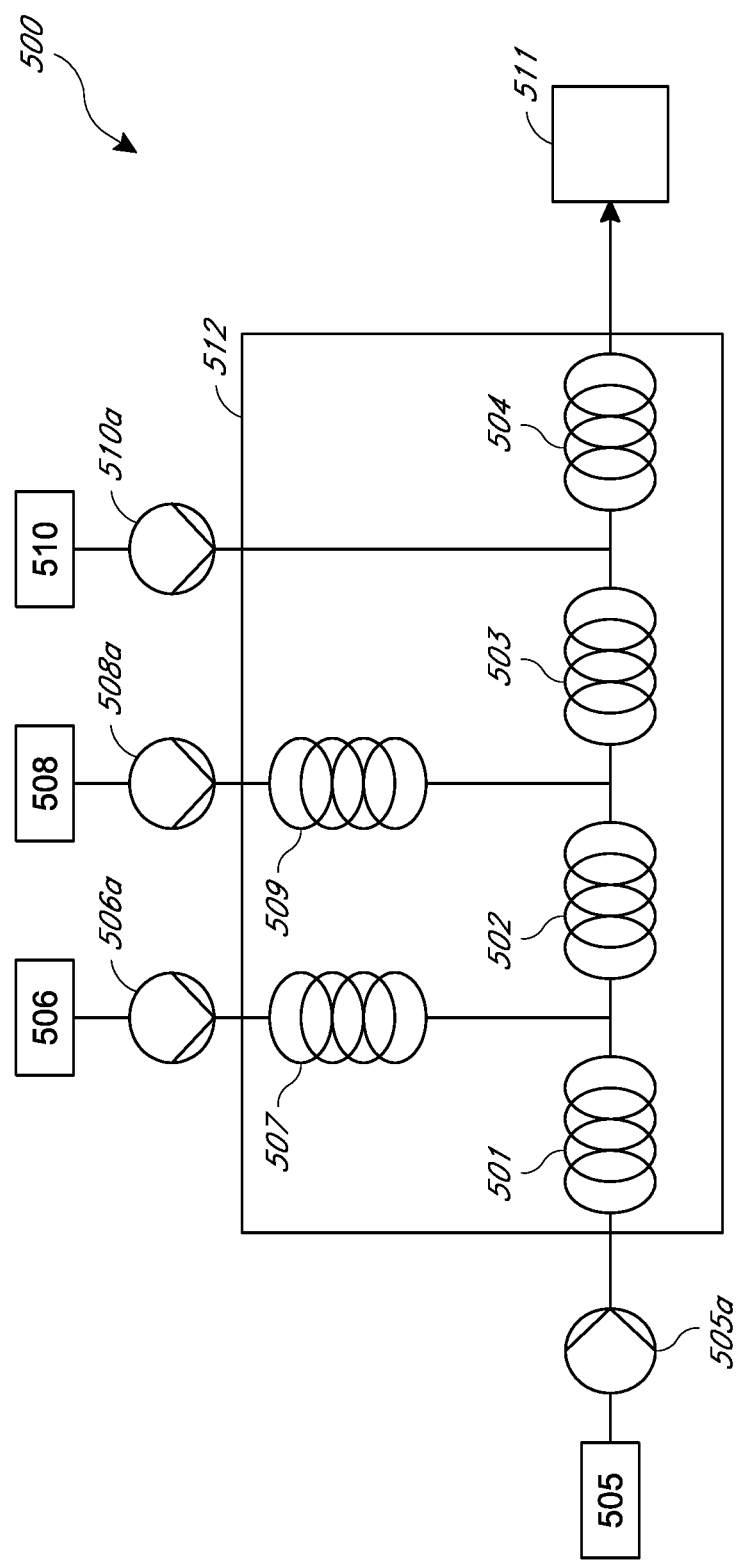
FIG. 6 shows an outlay of the continuous flow process apparatus used in Example 4.

The experimental set-up 500 used here is shown in FIG. 6. In FIG. 6, a continuous flow conduit 501 is used for delivering the n-butyl lithium solution, a continuous flow conduit 502 is used for mixing the n-butyl lithium and dichloromethane reagents and for delivering the reaction mixture to the next step, a continuous flow conduit 503 is used for combining the compound of Formula (IIa) or (IIb) and the reaction mixture that flows out of the continuous flow conduit 502, and a continuous flow conduit 504 is used for combining zinc chloride and the reaction mixture that flows out of the continuous flow conduit 503. During the reaction process, the n-butyl lithium stock solution was continuously added into the reaction process from the n-butyl lithium stock solution vessel 505 through a valve 505a and the n-butyl lithium was cooled in the continuous flow conduit 501 by using a cooling bath 512; a dichloromethane stock solution in THF was continuously added into the reaction process from the dichloromethane stock solution vessel 506 through a valve 506a and was pre-cooled to −15° C. in a continuous flow conduit 507; the mixture of n-butyl lithium and dichloromethane continuously flowed through the continuous flow conduit 502, which was cooled in the cooling bath 512; the stock solution of compound 1 was continuously added into the reaction process from the compound 1 stock solution vessel 508 through a valve 508a and was pre-cooled to −15° C. before being combined with the reaction mixture that flowed out of the continuous flow conduit 502 in the continuous flow conduit 503, which was cooled in the cooling bath 512; the zinc chloride stock solution in THF was continuously added into the reaction process from the zinc chloride stock solution vessel 510 through a valve 510a without pre-cooling and was later combined with the reaction mixture that flowed out the continuous flow conduit 503 in the continuous flow conduit 504; and the reaction mixture that flowed out of the continuous flow conduit 504 was then collected in a collection vessel 511. The continuous flow conduit 504, in which the zinc chloride was introduced and combined with the reaction mixture from the continuous flow conduit 503, was kept in the cooling bath 512. As illustrated in FIG. 5, a valve such as 505a, 506a, 508a, or 510a can be used to fluidly couple an output of a vessel to an input of a continuous flow conduit.

The starting materials were kept under nitrogen atmosphere and dry solvents (KF<0.01%) were used to prepare the stock solutions. The continuous flow set-up used here was made of stainless steel and was built using 1/16" spiraled tubing (internal diameter: 1 mm). The system was controlled using four Gilson 307 HPLC pumps, temperature control was achieved using a cooling bath with different compositions to maintain the desired reaction temperature.

Using the reaction parameters listed in Tables 2a and 2b, a constant conversion of compound 1 of 90% (based on HPLC area %) was achieved with the experimental set-up 500.

TABLE 2a

Experimental conditions for Comparative Example 4

| Stock solutions | | Flow | | |
| --- | --- | --- | --- | --- |
| | [ml] | [ml/min] | [mmol/min] | Equivalent |
| 1.6M n-BuLi in hexane | 10 | 1 | 0.914 | 1.37 |
| THF | 7.5 | | | |
| $CH_2Cl_2$ | 15 | 0.608 | 2.856 | 4.27 |
| THF | 35 | | | |
| Compound 1 | 10(g) | 1.403 | 0.668 | 1.00 |
| Heptane | 35 | | | |
| 0.5M $ZnCl_2$ in THF | | | | 1.11 |

TABLE 2b

Residence time for Comparative Example 4

| | Section # of set-up 500 | | | |
| --- | --- | --- | --- | --- |
| | 501 | 502 | 503 | 504 |
| Residence time (s) | 10 | 20 | 20 | 10 |

Figure 7:
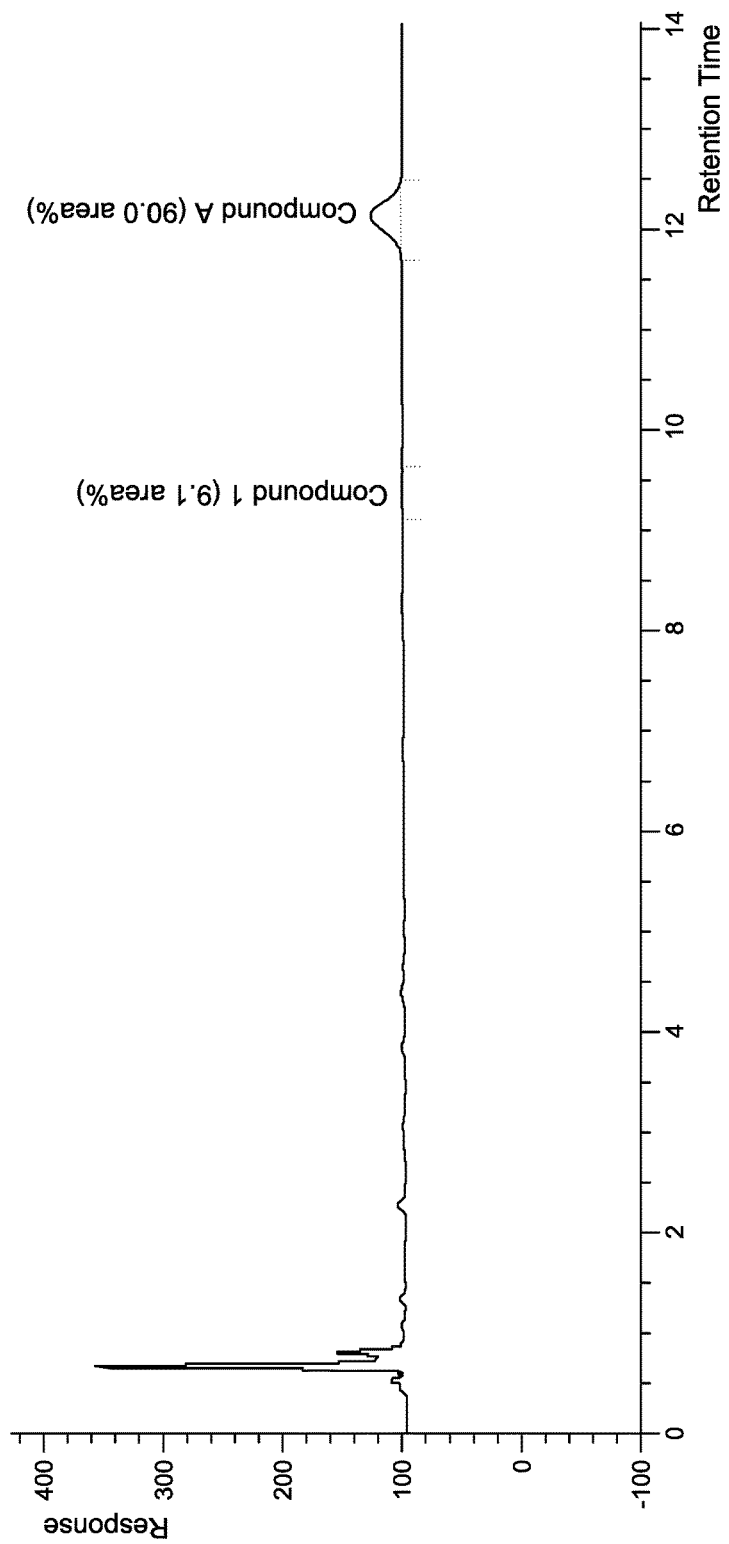
FIG. 7 shows the HPLC of Matteson reaction in Example 2.
Figure 8:
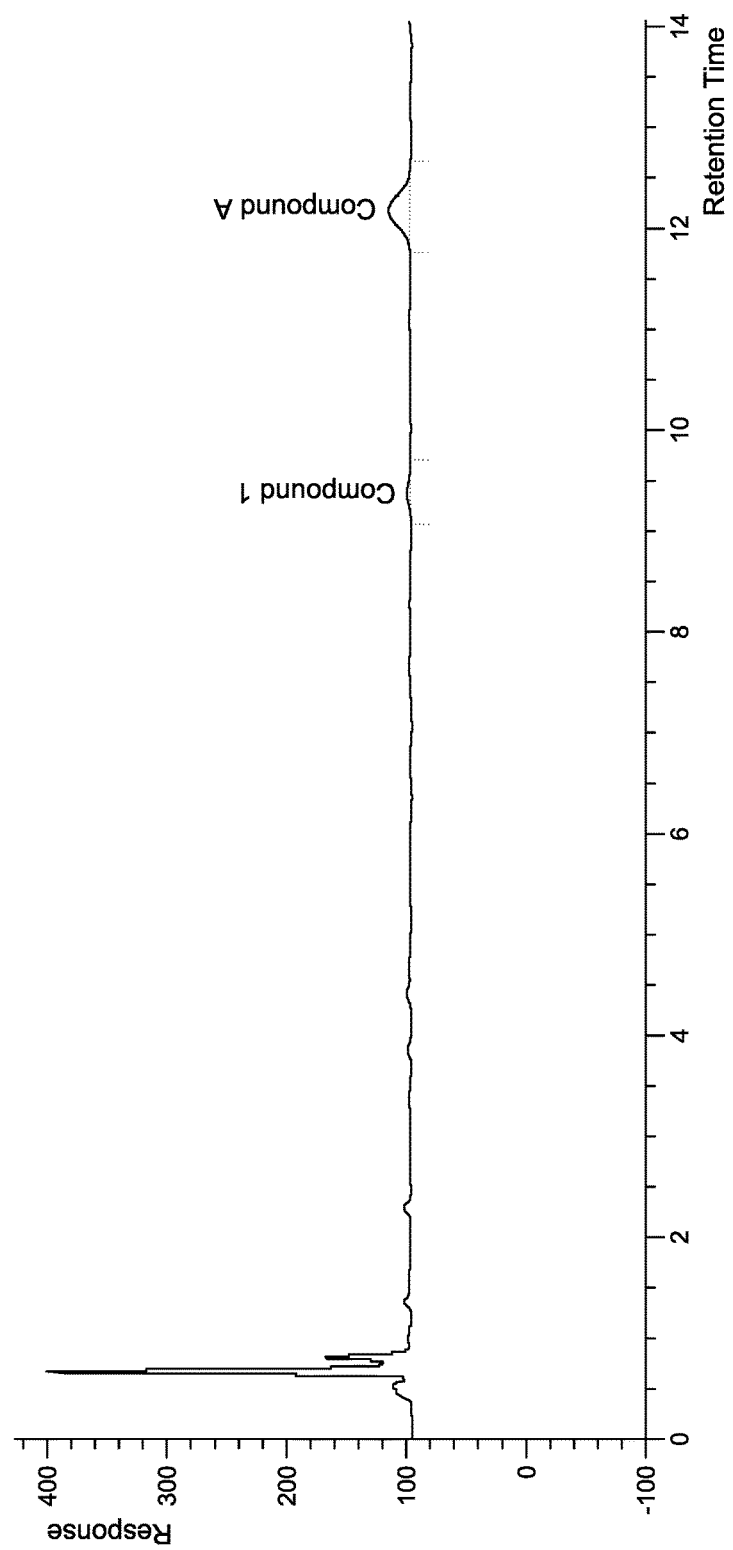
FIG. 8 shows the HPLC trace of the Matteson reaction in Example 2 using fresh stock solutions.

The reproducibility of the continuous flow reaction process was supported by the HPLC chromatograms shown in FIGS. 7 and 8. The parameters for achieving 90% conversion using the continuous flow set-up 500 is listed in Table 3.

TABLE 3

Reaction parameters for the continuous flow process in Example 4

| | |
|---|---|
| Total flow | 4.347 ml/min |
| Compound 1 concentration: | 13.343% (v/v) |
| Conversion | 90% |
| Output of Compound A | 0.601 mmol/min (0.318 g/min) |

In order to establish the yield of the reaction, 10 ml mixture was collected (run time 2.3 minutes) and concentrated in vacuo, yielding 0.73 g oil. The quantitative 1H-NMR with p-nitrotoluene as internal standard revealed an assay of 93% w/w. Consequently the total yield of compound A amounted to 0.68 g (1.32 mmol; 86%). Analysis revealed a diastereomeric ratio for this sample of 89:11, which was typical when applying 1.1 equivalents of zinc chloride. Increasing the amount of zinc chloride to two equivalents resulted in clogging of the continuous flow set-up.

Example 5

The experimental set-up as schematically outlined in FIG. 1 was used. As shown in FIG. 1, a continuous flow conduit 001 is used for cooling and delivering the n-butyl lithium solution, a continuous flow conduit 002 is used for combining the n-butyl lithium and dichloromethane reagents and for continuously delivering the reaction mixture to the next step, a continuous flow conduit 003 is for used combining the compound of formula (IIa) or (IIb) and the reaction mixture that flows out of the continuous flow conduit 002. The zinc chloride solution is not introduced into a continuous flow conduit. Instead, the reaction stream flowing out of the continuous conduit 003 is quenched in a vessel 010 containing a pre-cooled (−20° C.) zinc chloride solution (>2 equivalents).

During the reaction process, the n-butyl lithium stock solution was pre-cooled to −20° C. prior to being continuously added into the reaction process from a n-butyl lithium stock solution vessel 004 through a valve 004a and the n-butyl lithium was cooled in the continuous flow conduit 001 by using a cooling bath 009; a dichloromethane stock solution in THF was continuously added into the reaction process from a dichloromethane stock solution vessel 005 through a valve 005a and was cooled to −60° C. in a continuous flow conduit 006, which was placed in the cooling bath 009; the mixture of n-butyl lithium and dichloromethane continuously flowed through the continuous flow conduit 002, which was cooled in the cooling bath 009; the stock solution of compound 1 was continuously added into the reaction process from a compound 1 stock solution vessel 007 and was cooled to −60° C. before being combined with the reaction mixture that flowed out of the continuous flow conduit 002 in the continuous flow conduit 003, and the continuous flow conduit 003 was placed in the cooling bath 009; the reaction mixture that flowed out of the continuous flow conduit 003 was quenched in the fourth vessel 010, which contained a pre-cooled (−20° C.) zinc chloride solution (>2 equivalents). For work up, the quenched mixture was warmed to ambient temperature and washed twice with 1M HCl followed by two washes with water. The product solution was concentrated by distillation under vacuum to a defined volume, diluted with THF and again concentrated by distillation under vacuum to a defined volume to remove present water. The compound A was obtained in THF as the final product. The n-butyl lithium stock solution vessel 004 was fluidly coupled to the input of the continuous flow conduit 001 through a valve 004a. The dichloromethane stock solution vessel 005 was fluidly coupled to the continuous flow conduit 006 through a valve 005a. The compound 1 stock solution vessel 007 was fluidly coupled to the continuous flow conduit 008 through a valve 007a.

The stock solution of nBuLi (7.4 wt %) was prepared by diluting a 2.8M nBuLi solution in heptane with THF. For example, a flask was added with 40 mL (35.5 g) THF under inter gas protection and then cooled to <−60° C., then 14.4 g (20.3 mL) of a 2.8 M (25.6 wt %) nBuLi solution in heptane was added into the flask while keeping the temperature below −60° C. The stock solution of dichloromethane (39.0%) in THF was prepared by mixing 90.0 ml (119.3 g) dichloromethane in 210 ml (186.3 g) THF. The stock solution of compound 1 was prepared by first preparing a compound 1 (77.9 g) solution in heptane (38.0 wt % of compound 1) and then adding 24.1 g of THF (density 0.813 g/ml). The stock solution of Zinc chloride (9.7 wt %, 0.7 M) in THF was prepared by dissolving 22.2 g of zinc chloride in 233 ml (206.7 g) of THF.

TABLE 4

Reaction Conditions for the continuous flow process

| | |
|---|---|
| Cooling bath temperature | −60° C. |
| Flow rate of n-BuLi solution | 2.0 ml/min (1.0 eq) |
| Flow rate of dichloromethane solution | 1.2 ml/min (3.0 eq) |
| Flow of compound 1 solution | 3.2 ml/min (0.86 eq. = 1.17 eq nBuLi) |

The flow rates shown in Table 4 correspond to 21 seconds of residence time in the continuous flow conduit 002 and 23 seconds of residence time in the continuous flow conduit 003.

When starting the set-up, the dichloromethane flow was started first, followed by starting the flow of the compound 1 solution, and then followed by starting of the n-BuLi solution. A pre-run of 7 min to 10 min was performed and the reaction mixture from the pre-run and flowed through the continuous flow conduit 003 was collected, and then the reaction mixture flowing from the continuous flow conduit 003 was allowed to flow into 90 ml of zinc chloride solution (at about −20° C.) for 15 min. The amount of Zinc chloride corresponded to more than 2.1 mol equivalent of compound 1. Regular IPC samples were taken to check conversion and side product information, and the compound 1 flow can be changed based on the IPC results. IPC was determined based on the area % of compound 1, compound A, and side product in the HPLC chromatogram.

The reaction mixture in the zinc chloride vessel can be later washed twice with 1M HCL (46 ml for each wash), and then washed with water twice (46 ml for each wash). The obtained solution was concentrated by distillation under vacuum at a temperature (less than 50° C.) to be less than about 17 ml. 20 mL of THF was added to the distilled product, and the solution was distilled again under vacuum to about 30 ml. The water content was examined by KF titration, and if the water content was not less than 0.1%, additional distillation cycle was performed to reduce the water content. The weight of the final product solution was measured by taking an aliquot of the product solution and concentrating the product solution to an oil, followed by degassing the oil for 30 min at 10 mbar and 50° C. and calculating the percentage of compound A in the product solution based on the ratio of the product oil weight to the weight of the aliquot.

The continuous flow apparatus 050 was made of stainless steel and built using 1/16" spiraled tubing (internal diameter: 1 mm). The additions of dichloromethane and the compound 1 solutions were controlled using four Gilson 307 HPLC pumps with internal damper, the addition of n-butyl lithium solution was controlled using Harvard App Syringe Pump 11 Plus, and the temperature control was achieved using a cooling bath Haake KT900W Cryostat to achieve the desired reaction temperature. Some of the parameters for the continuous flow set-up 800 is listed in Table 5.

The continuous flow conduit 002 was 142 cm, twice-longer than the continuous flow conduit 102 in FIG. 2 and the continuous flow conduit 502 in FIG. 6, and the continuous flow conduit 003 was 315 cm, twice longer than the continuous flow conduit 103 in FIG. 2 and the continuous flow conduit 503 in FIG. 6. The flow rate in the continuous flow conduit 002 and the continuous flow conduit 003 were also twice faster than the flow rate in the continuous flow conduits 102 and 103 in FIG. 2 and the continuous flow conduits 502 and 503 in FIG. 6. The double flow and double spiral length provided better reproducibility and higher conversion. In addition, the molar equivalent of n-BuLi was reduced from 1.37 to 1.16, which allowed the process to be performed at higher temperature in the range of −65° C. to −60° C. In this way, reproducible results were obtained with over 99% conversion (typically <1% of compound 1 remaining). Depending on the amount of n-butyl lithium use, about d 1-3% of side product was observed. The diastereomeric excess of compound A produced in this set-up was higher than 95:5.

TABLE 5

Parameters for the continuous flow set-up in Example 1

| Section # of set-up 800 | Length (m) | Volume (ml) | Residence time (s) |
| --- | --- | --- | --- |
| 802 | 1.42 | 1.12 | 21 |
| 802 | 3.15 | 2.47 | 23 |
| Total | 4.57 | 3.59 | 44 |
| Output of Compound A (mg/min) | | 835 (based on calculation) | |

It has been demonstrated that a continuous flow process for the production of compound A has good reproducibility and provides a high yield (>70%) and high selectivity (diastereomers ratio >95:5). By performing all reaction steps in the continuous flow conduits but conducting the last step of quenching in a non-continuous flow reaction vessel, the continuous flow process described here has provided unexpected great reproducibility, reaction yield, and reaction selectivity as compared to the batch experiments in Comparative Example 1 and the continuous flow processes described in the Examples 1 to 4. The continuous processes described in the Examples 1 to 4 have all used a continuous flow conduit for each step of the Matteson reaction, including the last step of quenching with zinc chloride, but the Examples 1 to 4 did not provide a production process with good reproducibility and high yield. In addition, the batch process described in the Comparative Example 1 also has failed to provide a production process with a good yield. Therefore, it was unexpected that using a continuous flow process to produce an interaction intermediate while conducting the last step of quenching in a non-continuous-flow reaction vessel could have resulted in a production process with good reproducibility, high yield, and high selectivity.

Example 6

This continuous flow process described in Example 5 has been implemented successfully to produce 180 kg of compound A, thus demonstrating the scalability of the process.

In the large scale production, preparation of reaction solutions included: a solution of compound 1 (29 wt %) in heptane/THF was prepared by mixing 21.0 kg of compound 1 solution and diluting with 2.15 kg heptane and 20.2 kg of THF; a solution of DCM (39 wt %) in THF was prepared by mixing 17.8 kg DCM with 27.9 kg of THF; 0.7 M zinc chloride solution was prepared by dissolving 17.51 kg $ZnCl_2$ in 163 kg THF; and n-BuLi stock solution in heptane/THF was prepared by cooling 44 kg of THF to −60° C. and subsequently mixing with 17.5 kg n-Buli solution in heptane in 40 min at about −60° C.

The continuous flow process was conducted using the following steps: the continuous flow conduits were cooled to −60 to −70° C. and the n-BuLi/THF flow was started at 7 kg/h for about 20 min until the temperature of the flow reached −25° C. Then the flow was adjusted to 2.55 kg/h. The compound 1/Heptane/THF flow was started at 3.97 kg/h. After about 15 min the DCM/THF flow was started at 1.4 kg/h. After 30 min, the reaction mixture formed following quenching in the $ZnCl_2$ solution (precooled to −20° C.) was collected. After the reaction mixture was collected for 4 hrs, the compound 1/Heptane/THF flow was adjusted to 3.91 kg/h based on IPC results. After a total of 15 hours of collection time, a second flask with fresh the zinc chloride was used for collection. After collecting of the reaction mixture for 15 h, collection was continued for additional 5.5 hr in another vessel with fresh Zinc chloride added. Once the IPC results confirmed the completion of the reaction, the solutions from the quenching step were combined and then washed twice with 114.5 kg HCl (3.4%) used for each. Subsequently the organic phase was washed twice with 113 kg of water used for each wash. The product solution was concentrated by distillation under vacuum at a temperature of less than 50° C. to about 40 L. 48.5 kg THF were added and the obtained solution was again concentrated by distillation under vacuum at a temperature of less 50° C. to about 55 L. The water content of 0.02% was determined by KF titration. The product solution was transferred into a steel drum. 43.5 kg of product solution was collected, which showed a content of 58.2 wt % compound A by distillation to an oil.

TABLE 6

Reaction parameters for large scale productions

| | Compound 1 | Output | | Yield |
| --- | --- | --- | --- | --- |
| Experiment # | Input (Kg) | Kg | HI | as is |
| 1 | 13.90 | 15.20 | 95.6% | 99.1% |
| 2 | 13.90 | 15.36 | 97.4% | 100.1% |
| 3 | 13.90 | 15.30 | 96.7% | 99.7% |
| 4 | 24.8 | 25.6 | 94.8% | 93.5% |
| 5 | 49.60 | | | |
| 6 | | 25.6 | 95.0% | 93.5% |

TABLE 6-continued

Reaction parameters for large scale productions

| Experiment # | Compound 1 Input (Kg) | Output Kg | HI | Yield as is |
|---|---|---|---|---|
| 7 | 24.80 | 25.30 | 94.6% | 92.4% |
| 8 | 48.64 | 24.35 | 94.7% | 88.9% |
| 9 | | 24.90 | 95.1% | 91.0% |
| 10 | 36.20 | 24.40 | 95.4% | 89.1% |
| 11 | | 29.90 | 94.1% | 76.9% |
| Total/average | 184.04 | 180.05 | | 88.6% |

Example 7

Figure 9:
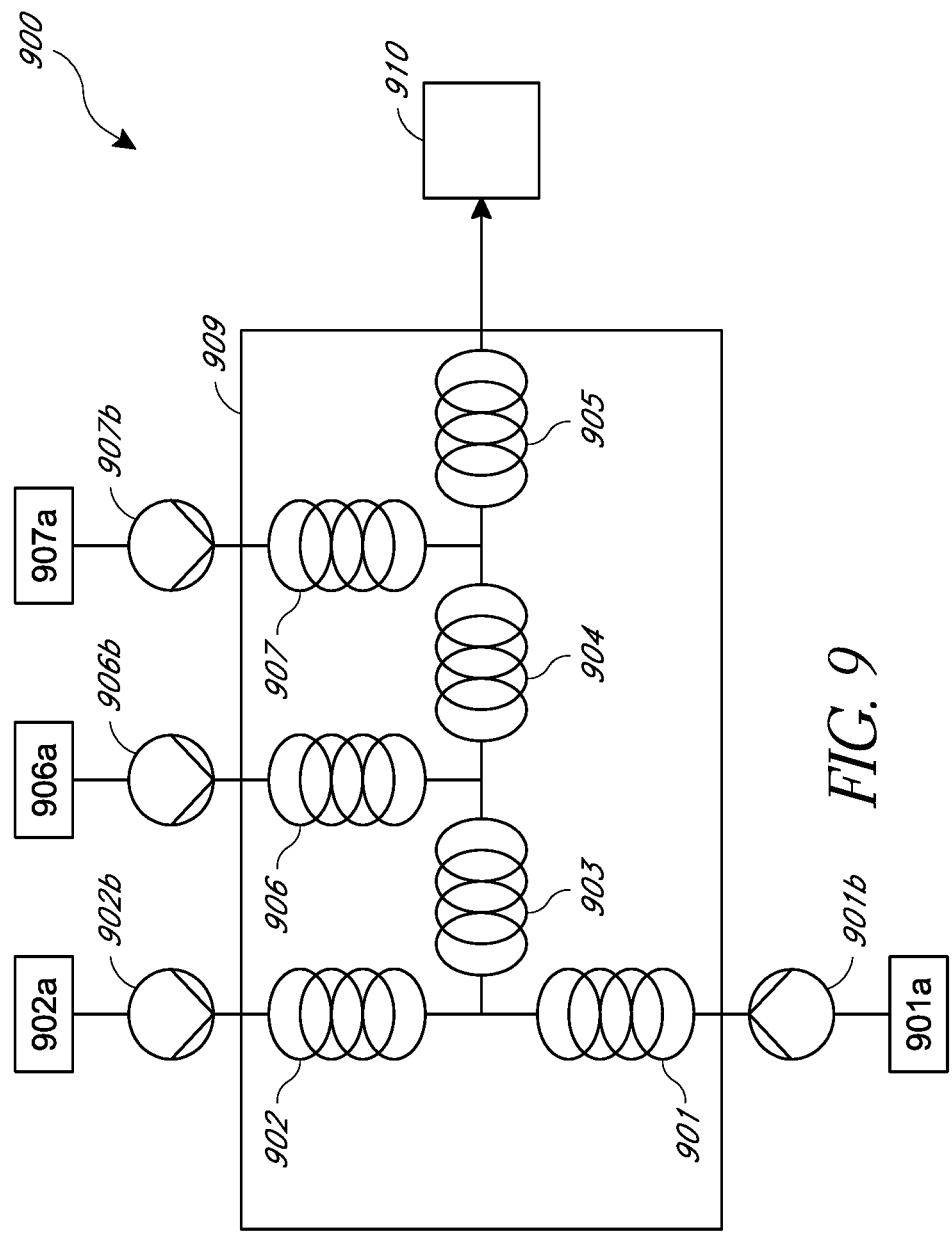
FIG. 9 is a schematic of the continuous flow process used in Example 7.

The experimental set-up 900 as schematically outlined in FIG. 9 was used. As shown in FIG. 9, a continuous flow conduit 901 is used for delivering butyl lithium in heptane stock solution, and a continuous flow conduit 902 is used for delivering tetrahydrofuran stock solution. During the process, the continuous stream of butyl lithium in heptane and the continuous stream of tetrahydrofuran were combined at an input of a continuous flow conduit 903. The stock solution of butyl lithium in heptane was stored in a vessel 901a, and the stock solution of tetrahydrofuran was stored in a vessel 902a. The stock solution of dichloromethane was stored in a vessel 906a, and a continuous flow conduit 906 was used to deliver dichloromethane to the input of the continuous flow conduit 904. The combined mixture of the butyl lithium in tetrahydrofuran and heptane flowing out of the continuous flow conduit 903 was combined with the continuous flow of dichloromethane at the input of a continuous flow conduit 904. The reaction intermediate flowing out of the output of the continuous flow conduit 904 was combined with the compound of Formula (IIa) or (IIb) at the input of a continuous flow conduit 905. The compound of Formula (IIa) or (IIb) in heptane was stored in a vessel 907a and delivered to the input of the continuous flow conduit 905 through a continuous flow conduit 907. The reaction intermediate flowing out of the output of the continuous flow conduit 905 was then collected in a vessel 910 which contained zinc chloride. The continuous flow conduits 901-907 were placed in a cooling bath 909, and the vessel 910 was also placed in a cooling bath. The vessel 901a was fluidly coupled to the continuous flow conduit 901 through a valve 901b; the vessel 902a was fluidly coupled to the continuous flow conduit 902 through a valve 902b; the vessel 906a was fluidly coupled to the continuous flow conduit 906 through a valve 906b; and the vessel 907a was fluidly coupled to the continuous flow conduit 907 through a valve 907b. The vessels 901a, 902a, 906a, and 907a were pressurized vessels. The flow rates of the various reagents flowing out of the vessels were adjusted through the corresponding valves 901b, 902b, 906b, and 907b.

The continuous flow set-up used in Example 7 can be made of stainless steel spiraled tubing. The continuous flow conduits 901 and 902 was about 0.5 m long, the continuous flow conduit 903 was 6 m long, the continuous flow conduit 904 was in the range of about 1.5 m to 3 m long, the continuous flow conduit 905 was about 6 m long, the continuous flow conduit 906 was about 0.5 m long, and the continuous flow conduit 907 was about 0.5 m long. Table 7 shows the reaction parameters used in the continuous flow process. The tubing length and diameters can be adjusted based on the experiments scale and reaction conditions. The relative molar ratio of n-butyl lithium to Compound 1 as listed in the table can have a maximum deviation of 0.2.

TABLE 7

The continuous flow process was conducted using the following parameters:

| Parameter | Set-point |
|---|---|
| Concentration of Compound 1 solution [%] | 38.0 |
| Concentration of Compound 1 in THF [%] | 29.0 |
| Flow rate of Compound 1 [g/min] | 3.2 |
| Flow rate of Compound 1 [mmol/min] | 2.0 |
| Concentration n-BuLi solution [%] | 25.0 |
| Flow rate of n-BuLi solution [g/min] | 0.7 |
| Flow rate of n-BuLi [mmol/min] | 2.7 |
| Molar ratio of n-BuLi to Compound 1 | 1.4 |
| Concentration of dichloromethane in THF [%] | 39 |
| relative molar ratio of dichloromethane to n-BuLi | 3 |
| Amount of Zinc chloride | 0.70 kg $ZnCl_2$/kg compound of formula (IIa) or (IIb) |
| Molar ratio of $ZnCl_2$ to Compound 1 | 2.4 |
| Concentration of $ZnCl_2$ in THF [%] | 11.8 |
| Temperature of $ZnCl_2$ in THF solution (° C.) | −25° C. |
| Temperature for cooling bath 1011 | −75° C. |

IPC was used to determine the reaction conversion, and the reaction solution was evaluated based on the presence of the compound of formula (IIa) or (IIb) or the presence of a chlorine side product. When the amount of the compound of formula (IIa) or (IIb) exceeded the limit, the n-BuLi flow was increased. When the amount of the chlorine side product exceeded the limit, the n-BuLi flow was decreased.

The reaction intermediate that was treated with $ZnCl_2$ were then purified through extraction and distillation. The first extraction was performed using 1M HCL without delay due to the stability of the extracted product. The compound (Ia) or (Ib) assay was decreasing significantly within 24 h. The impurity profile was almost unchanged. The second extraction was performed using 1M HCl at room temperature. The third extraction was performed using 5% $NaHCO_3$ to neutralize the HCl as all the protection groups are acid labile. The fourth extraction was performed with water at room temperature. The product from the fourth extraction was fairly stable at room temperature. After the fourth extraction, the product underwent distillation at a reduced pressure at 50° C. The continuous flow process for the production of compound A described in Example 7 has achieved good reproducibility and provided high yield and high selectivity.

Example 8

Several large scale productions were performed using the process described in Example 7. The reaction parameters have been scaled proportionally based on the amount of starting materials. The production results for compound B are summarized in Table 8 below. The continuous flow process described in Example 7 was used to produce more than 880 kg of Compound A under full cGMP, thus demonstrating the successful application of the process described herein in a large scale pharmaceutical production.

TABLE 8

Large scale production using the continuous process in Example 7.

| No. | Solution isolated (kg) | Yield (%) | Total impurities (area %) |
|---|---|---|---|
| 1 | 162 | 91 | 2.0 |
| 2 | 164 | 95 | 1.6 |
| 3 | 160 | 89 | 2.0 |
| 4 | 156 | 94 | 1.5 |
| 5 | 153 | 93 | 1.6 |
| 6 | 151 | 93 | 1.6 |
| 7 | 153 | 92 | 1.7 |
| 8 | 154 | 94 | 1.5 |
| 9 | 139 | 91 | 1.3 |
| 10 | 160 | 92 | 1.1 |
| 11 | 153 | 91 | 1.9 |
| 12 | 137 | 78 | 2.6 |

What is claimed is:

1. A process for production of a compound of Formula (Ia) or (Ib),

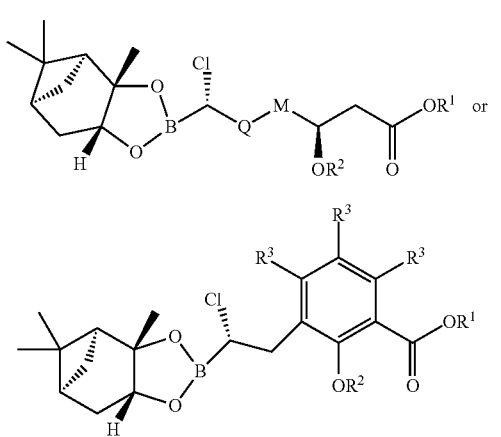

wherein:
Q is —$(CH_2)_n$—;
M is —$CH_2$— or —CH=CH—;
n is 1 or 2;
$R^1$ is a carboxyl protecting group;
$R^2$ is a hydroxyl protecting group; or
$R^1$ and $R^2$ together with the atoms to which they are attached form a heterocyclic ring optionally substituted with $C_{1-4}$ alkyl;
each $R^3$ is independently selected from hydrogen, —OH, halogen, —$CF_3$, $C_1$-$C_6$ alkenyl, $C_1$-$C_6$ alkynyl, $C_1$-$C_6$ heteroalkyl, $C_3$-$C_7$ carbocyclyl, 5-10 membered heterocyclyl, $C_{6-10}$ aryl, 5-10 membered heteroaryl, cyano, $C_1$-$C_6$ alkoxy($C_1$-$C_6$)alkyl, $C_{6-10}$ aryloxy, sulfhydryl (mercapto), and —$(CH_2)_m$—Y'—$(CH_2)_p$M';

m and p are independently 0 to 3;

Y' is selected from the group consisting of —S—, —S(O)—, —$S(O)_2$—, —O—, —$CR^{4a}R^{5a}$—, and —$NR^{1a}$—;

M' is selected from the group consisting of C(O)$NR^{1a}R^{2a}$; —C(O)$NR^{1a}OR^{3a}$; —$NR^{1a}$C(O)$R^{4a}$; —$NR^{1a}$C(O)$NR^{2a}R^{1b}$; —$NR^{1a}$C(O)$OR^{3a}$; $NR^1$S(O)$_2R^{3a}$; —$NR^{1a}$S(O)$_2NR^{2a}R^{1b}$; —C(=$NR^{1a}$)$R^{4a}$; —C(=$NR^{1a}$)$NR^{2a}R^{1b}$; —$NR^{1a}$C$R^{4a}$(=$NR^{2a}$); —$NR^{1a}$C(=$NR^{2a}$)$NR^{1b}R^{2b}$; $C_{1-4}$ alkyl optionally substituted with 0-2 substituents selected from the group consisting of —$OR^{3a}$, —$NR^{1a}R^{2a}$, halogen, —C(O)$NR^{1a}R^{2a}$, and —$NR^{1a}$C(O)$R^{4a}$; $C_{3-10}$ cycloalkyl optionally substituted with 0-2 substituents selected from the group consisting of $C_{1-4}$ alkyl, —$OR^{3a}$, —$NR^{1a}R^{2a}$, halogen, —C(O)$NR^{1a}R^{2a}$, and —$NR^{1a}$C(O)$R^{4a}$; $C_{6-10}$ aryl optionally substituted with 0-2 substituents selected from the group consisting of $C_{1-4}$ alkyl, —$OR^{3a}$, —$NR^{1a}R^{2a}$, halogen, —C(O)$NR^{1a}R^{2a}$, and —$NR^{1a}$C(O)$R^{4a}$; 5 to 10 membered heteroaryl optionally substituted with 0-2 substituents selected from the group consisting of $C_{1-4}$ alkyl, —$OR^{3a}$, —$NR^{1a}R^{2a}$; halogen, —C(O)$NR^{1a}R^{2a}$; and —$NR^{1a}$C(O)$R^{4a}$; and 4 to 10 membered heterocyclyl optionally substituted with 0-2 substituents selected from the group consisting of $C_{1-4}$ alkyl, —$OR^{3a}$, —$NR^{1a}R^{2a}$, halogen, —C(O)$NR^{1a}R^{2a}$, and —$NR^{1a}$C(O)$R^{4a}$;

each $R^{1a}$, $R^{2a}$, $R^{1b}$ and $R^{2b}$ are independently selected from the group consisting of —H, optionally substituted $C_{1-10}$alkyl, optionally substituted $C_{2-10}$alkenyl, optionally substituted $C_{2-10}$alkynyl, optionally substituted $C_{3-7}$ cycloalkyl, optionally substituted 3-8 membered heterocyclyl, optionally substituted $C_{6-10}$aryl, and optionally substituted 5-10 membered heteroaryl;

$R^{3a}$ is hydrogen, optionally substituted $C_{1-10}$alkyl, optionally substituted $C_{1-10}$alkyl-COOH, optionally substituted $C_{2-10}$alkenyl, optionally substituted $C_{2-10}$alkynyl, optionally substituted $C_{3-7}$ cycloalkyl, optionally substituted 3-8 membered heterocyclyl, optionally substituted $C_{6-10}$aryl, and optionally substituted 5-10 membered heteroaryl; and each $R^{4a}$ and $R^{5a}$ is independently selected from the group consisting of —H, —OH, —optionally substituted alkoxyl, optionally substituted $C_{1-10}$alkyl, optionally substituted $C_{2-10}$alkenyl, optionally substituted $C_{2-10}$alkynyl, optionally substituted $C_{3-7}$ cycloalkyl, optionally substituted 3-8 membered heterocyclyl, optionally substituted $C_{6-10}$aryl, and optionally substituted 5-10 membered heteroaryl;

the process comprising:

providing a first continuous flow of alkyl lithium;

providing a continuous flow of dichloromethane;

combining the first continuous flow of alkyl lithium and the continuous flow of dichloromethane at an input of a first continuous flow conduit to yield a continuous flow of a first reaction intermediate at an output of the first continuous flow conduit;

providing a continuous flow of a compound of Formula (IIa) or (IIb);

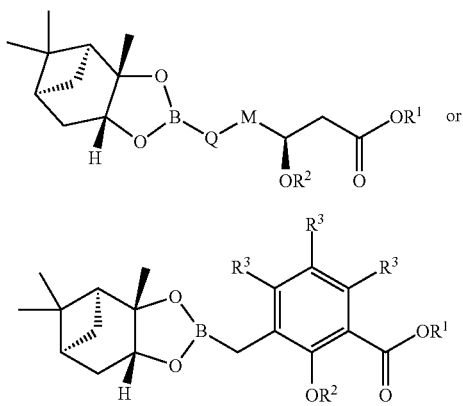

combining the continuous flow of the first reaction intermediate and the continuous flow of the compound of Formula (IIa) or (IIb) at an input of the a second continuous flow conduit to yield a second reaction intermediate at an output of the second continuous flow conduit;

collecting the second reaction intermediate at the output of the second continuous flow conduit; and treating the collected second reaction intermediate with a Lewis acid to yield the compound of Formula (Ia) or (Ib).

2. The process of claim 1, wherein the second reaction intermediate is collected into a vessel and the vessel does not have continuous outflow.

3. The process of claim 1, wherein the first continuous flow of alkyl lithium is a continuous flow of alkyl lithium in hexane and tetrahydrofuran.

4. The process of claim 1, wherein the providing a first continuous flow of alkyl lithium further comprises
providing a continuous flow of tetrahydrofuran;
providing a second continuous flow of alkyl lithium; and
combining the continuous flow of tetrahydrofuran and the second continuous flow of alkyl lithium at an input of a third continuous flow conduit to form the first continuous flow of alkyl lithium.

5. The process of claim 1, wherein the continuous flow of dichloromethane is a continuous flow of dichloromethane in tetrahydrofuran, and wherein the continuous flow of the compound of Formula (IIa) or (IIb) is a continuous flow of the compound of Formula (IIa) or (IIb) in heptane.

6. The process of claim 1, comprising preparing the alkyl lithium, the dichloromethane, and the compound of formula (IIa) or (IIb) under a nitrogen or argon atmosphere.

7. The process of claim 1, wherein the alkyl lithium, the dichloromethane, the compound of formula (IIa) or (IIb), and the Lewis acid are substantially free of water.

8. The process of claim 1, comprising pre-cooling at least one reagent selected from the alkyl lithium, the dichloromethane, and the compound of Formula (IIa) or (IIb) to a temperature in the range of about −80° C. to about −65° C. prior to the combining of the first continuous flow of alkyl lithium and the continuous flow of dichloromethane.

9. The process of claim 1, comprising pre-cooling the Lewis acid to a temperature of about −20° C. prior to the treating, and maintaining at least one of the first continuous flow conduit and the second continuous flow conduit at a temperature in the range of about −80° C. to about −65° C. during the process.

10. The process of claim 1, wherein a flow time from the input to the output of the first continuous flow conduit or the second continuous flow conduit is about 5 seconds to about 50 seconds.

11. The process of claim 1, wherein the molar ratio of alkyl lithium to dichloromethane is in the range of about 1:1 to about 1:10, wherein the molar ratio of alkyl lithium to the compound of Formula (IIa) or (IIb) is in the range of about 0.5:1 to about 5:1, and wherein the molar ratio of Lewis acid to the compound of Formula (IIa) or (IIb) is in the range of about 0.5:1 to about 5:1; and wherein the molar ratio of Lewis acid to the compound of Formula (IIa) or (IIb) is in the range of about 0.5:1 to about 5:1.

12. The process of claim 1, comprising flowing the alkyl lithium into the first continuous flow conduit at a flow rate of about 0.1 mmol/min to about 5.0 mmol/min, flowing the dichloromethane into the first continuous flow conduit at a flow rate of about 1 mmol/min to about 5 mmol/min, and flowing the compound of Formula (IIa) or (IIb) into the second continuous flow conduit at a flow rate of about 0.1 mmol/min to about 5 mmol/min.

13. The process of claim 1, wherein the treating of the second reaction intermediate with the Lewis acid is not performed in a continuous flow conduit.

14. The process of claim 1, further comprising at least one step selected from the group consisting of:
1) combining alkyl lithium in heptane and tetrahydrofuran to prepare an alkyl lithium stock solution for the first continuous flow of alkyl lithium and pressurizing a vessel comprising the alkyl lithium stock solution;
2) preparing a stock solution of alkyl lithium in heptane and pressurizing a vessel comprising the stock solution of alkyl lithium in heptane;
3) preparing a stock solution of tetrahydrofuran and pressurizing a vessel comprising the stock solution of tetrahydrofuran;
4) combining dichloromethane and tetrahydrofuran to provide a dichloromethane stock solution for the continuous flow of dichloromethane and pressurizing a vessel comprising the dichloromethane stock solution;
5) combining the compound of Formula (IIa) or (IIb) and heptane to provide a compound of Formula (IIa) or (IIb) stock solution and pressurizing a vessel comprising the compound of the Formula (IIa) or (IIb) stock solution; and
6) combining the Lewis acid and tetrahydrofuran to provide a Lewis acid stock solution and pressurizing a vessel comprising the Lewis acid stock solution.

15. The process of claim 14, comprising:
1) combining alkyl lithium in heptane and tetrahydrofuran to prepare an alkyl lithium stock solution for the first continuous flow of alkyl lithium and pressurizing a vessel comprising the alkyl lithium stock solution; 2) preparing a stock solution of alkyl lithium in heptane and pressurizing a vessel comprising the stock solution of alkyl lithium in heptane; 3) preparing a stock solution of tetrahydrofuran and pressurizing a vessel comprising the stock solution of tetrahydrofuran;
4) combining dichloromethane and tetrahydrofuran to provide a dichloromethane stock solution for the continuous flow of dichloromethane and pressurizing a vessel comprising the dichloromethane stock solution;
5) combining the compound of Formula (IIa) or (IIb) and heptane to provide a compound of Formula (IIa) or (IIb) stock solution and pressurizing a vessel comprising the compound of the Formula (IIa) or (IIb) stock solution; and 6) combining the Lewis acid and tetrahydrofuran to provide a Lewis acid stock solution and pressurizing a vessel comprising the Lewis acid stock solution.

16. The process of claim 1, wherein the alkyl lithium is n-butyl lithium and the Lewis acid is zinc chloride.

17. The process of claim 1, comprising producing the compound of Formula (Ia) and using the compound of Formula (Ia) to produce a β-lactamase inhibitor.

18. The process of claim 1, wherein M is —CH═CH— and n is 1, or wherein M is —CH$_2$— and Q is —CH$_2$— or —CH$_2$—CH$_2$—.

19. The process of claim 1, comprising producing a compound of Formula (Ib) and using the compound of Formula (Ib) to produce a β-lactamase inhibitor.

20. The process of claim 1, wherein R$^2$ is tert-butyldimethylsilyl, and R$^1$ is tert-butyl.

21. The process of claim 1, wherein the compound of Formula (Ib) has a structure of Formula (III):

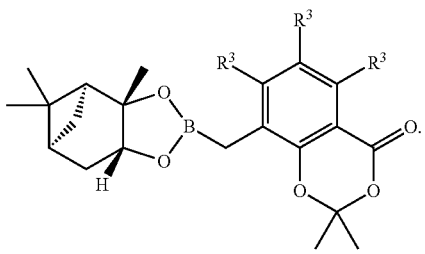

(III)

22. The process of claim 1, wherein the compound of Formula (Ia) is

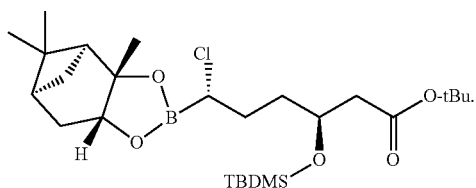

23. The process of claim 1, wherein the compound of Formula (IIa) is

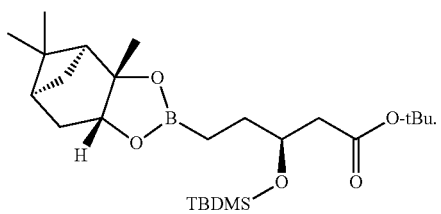

24. An apparatus for production of a compound of Formula (Ia) or (Ib),

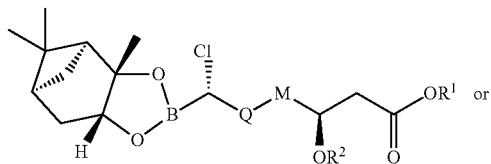

(Ia)

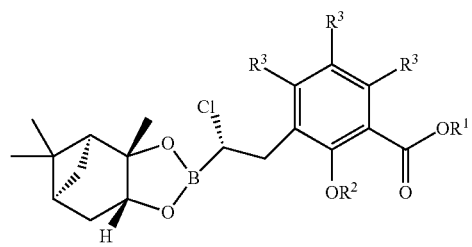

(Ib)

wherein:
Q is —(CH$_2$)$_n$—;
M is —CH$_2$— or —CH═CH—;
n is 1 or 2;
R$^1$ is a carboxyl protecting group;
R$^2$ is a hydroxyl protecting group; or
R$^1$ and R$^2$ together with the atoms to which they are attached form a heterocyclic ring optionally substituted with C$_{1-4}$ alkyl;
each R$^3$ is independently selected from hydrogen, —OH, halogen, —CF$_3$, C$_1$-C$_6$ alkenyl, C$_1$-C$_6$ alkynyl, C$_1$-C$_6$ heteroalkyl, C$_3$-C$_7$ carbocyclyl, 5-10 membered heterocyclyl, C$_{6-10}$ aryl, 5-10 membered heteroaryl, cyano, C$_1$-C$_6$ alkoxy(C$_1$-C$_6$)alkyl, C$_{6-10}$ aryloxy, sulfhydryl (mercapto), and —(CH$_2$)$_m$—Y'—(CH$_2$)$_p$M';
m and p are independently 0 to 3;
Y' is selected from the group consisting of —S—, —S(O)—, —S(O)$_2$—, —O—, —CR$^{4a}$R$^{5a}$—, and —NR$^{1a}$—;
M' is selected from the group consisting of —C(O)NR$^{1a}$R$^{2a}$; —C(O)NR$^{1a}$OR$^{3a}$; —NR$^{1a}$C(O)R$^{4a}$; —NR$^{1a}$C(O)NR$^{2a}$R$^{1b}$; —NR$^{1a}$C(O)OR$^{3a}$; S(O)$_2$R$^{3a}$; —NR$^{1a}$S(O)$_2$NR$^{2a}$R$^{1b}$; —C(═NR$^{1a}$)R$^{4a}$; —C(═NR$^{1a}$)NR$^{2a}$R$^{1b}$; —NR$^{1a}$CR$^{4a}$(═NR$^{2a}$); —NR$^{1a}$(═NR$^{2a}$)NR$^{1b}$R$^{2b}$; C$_{1-4}$ alkyl optionally substituted with 0-2 substituents selected from the group consisting of —OR$^{3a}$, —NR$^{1a}$R$^{2a}$, halogen, —C(O)NR$^{1a}$R$^{2a}$, and —NR$^{1a}$C(O)R$^{4a}$; C$_{3-10}$ cycloalkyl optionally substituted with 0-2 substituents selected from the group consisting of C$_{1-4}$ alkyl, —OR$^{3a}$, —NR$^{1a}$R$^{2a}$, halogen, —C(O)NR$^{1a}$R$^{2a}$, and —NR$^{1a}$C(O)R$^{4a}$; C$_{6-10}$ aryl optionally substituted with 0-2 substituents selected from the group consisting of C$_{1-4}$ alkyl, —OR$^{3a}$, —NR$^{1a}$R$^{2a}$, halogen, —C(O)NR$^{1a}$R$^{2a}$, and —NR$^{1a}$C(O)R$^{4a}$; 5 to 10 membered heteroaryl optionally substituted with 0-2 substituents selected from the group consisting of C$_{1-4}$ alkyl, —OR$^{3a}$, —NR$^{1a}$R$^{2a}$, halogen, —C(O)NR$^{1a}$R$^{2a}$, and —NR$^{1a}$C(O)R$^{4a}$; and 4 to 10 membered heterocyclyl optionally substituted with 0-2 substituents selected from the group consisting of C$_{1-4}$ alkyl, —OR$^{3a}$, —NR$^{1a}$R$^{2a}$, halogen, —C(O)NR$^{1a}$R$^{2a}$, and —NR$^{1a}$C(O)R$^{4a}$;
each R$^{1a}$, R$^{2a}$, R$^{1b}$ and R$^{2b}$ are independently selected from the group consisting of —H, optionally substituted C$_{1-10}$alkyl, optionally substituted C$_{2-10}$alkenyl, optionally substituted C$_{2-10}$alkynyl, optionally substituted C$_{3-7}$ cycloalkyl, optionally substituted 3-8 membered heterocyclyl, optionally substituted $C_{6-10}$aryl, and optionally substituted 5-10 membered heteroaryl;

$R^{3a}$ is hydrogen, optionally substituted $C_{1-10}$alkyl, optionally substituted $C_{1-10}$alkyl-COOH, optionally substituted $C_{2-10}$alkenyl, optionally substituted $C_{2-10}$alkynyl, optionally substituted $C_{3-7}$ cycloalkyl, optionally substituted 3-8 membered heterocyclyl, optionally substituted $C_{6-10}$aryl, and optionally substituted 5-10 membered heteroaryl; and each $R^{4a}$ and $R^{5a}$ is independently selected from the group consisting of —H, —OH, —optionally substituted alkoxyl, optionally substituted $C_{1-10}$alkyl, optionally substituted $C_{2-10}$alkenyl, optionally substituted $C_{2-10}$alkynyl, optionally substituted $C_{3-7}$ cycloalkyl, optionally substituted 3-8 membered heterocyclyl, optionally substituted $C_{6-10}$aryl, and optionally substituted 5-10 membered heteroaryl;

the apparatus comprising:

a first vessel having an output and comprising alkyl lithium;

a second vessel having an output and comprising dichloromethane;

a first continuous flow conduit comprising an input and an output, wherein the input of the first continuous flow conduit is fluidly coupled to the output of the first vessel and the output of the second vessel;

a third vessel having an output and comprising a compound of Formula (IIa) or (IIb);

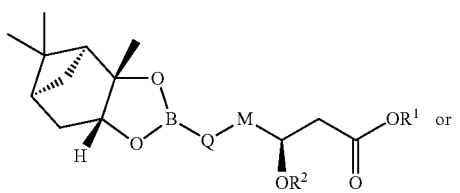
(IIa)

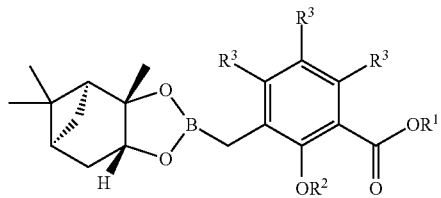
(IIb)

a second continuous conduit comprising an input and an output, wherein the input of the second continuous conduit is fluidly coupled to the output of the first continuous flow conduit and the output of the third vessel; and a fourth vessel having an input fluidly coupled to the output of the second continuous flow conduit and comprising a Lewis acid.

25. The process of claim 22, comprising using

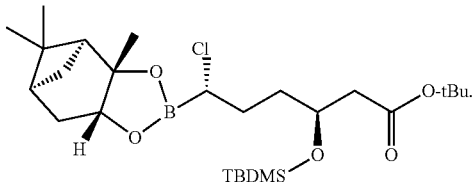

to produce

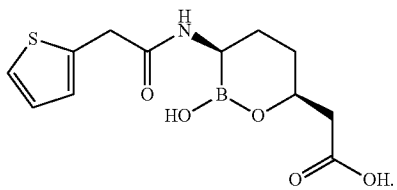 [SMILES: O=C(O)C[C@@H]1CC[C@H](NC(=O)Cc2cccs2)B(O)O1]

* * * * *

UNITED STATES PATENT AND TRADEMARK OFFICE
CERTIFICATE OF CORRECTION

PATENT NO. : 10,364,257 B2  
APPLICATION NO. : 15/537378  
DATED : July 30, 2019  
INVENTOR(S) : Ulfried Felfer et al.

Page 1 of 1

It is certified that error appears in the above-identified patent and that said Letters Patent is hereby corrected as shown below:

On the Title Page

Item (71) should be corrected to read:
(71) Applicant: Rempex Pharmaceuticals, Inc., Lincolnshire, IL (US)

Signed and Sealed this
Twenty-ninth Day of October, 2019

Andrei Iancu
*Director of the United States Patent and Trademark Office*